(12) United States Patent
Buck et al.

(10) Patent No.: US 9,658,208 B2
(45) Date of Patent: May 23, 2017

(54) METHODS AND G PROTEINS FOR SCREENING AND IDENTIFYING LIGANDS OF G PROTEIN-COUPLED RECEPTORS

(71) Applicant: Fred Hutchinson Cancer Research Center, Seattle, WA (US)

(72) Inventors: Linda Buck, Seattle, WA (US); Stephen D. Liberles, Wellesley, MA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 54 days.

(21) Appl. No.: 14/367,731

(22) PCT Filed: Dec. 21, 2012

(86) PCT No.: PCT/US2012/071412
§ 371 (c)(1),
(2) Date: Jun. 20, 2014

(87) PCT Pub. No.: WO2013/096859
PCT Pub. Date: Jun. 27, 2013

(65) Prior Publication Data
US 2015/0018233 A1    Jan. 15, 2015

Related U.S. Application Data

(60) Provisional application No. 61/579,316, filed on Dec. 22, 2011.

(51) Int. Cl.
*C12Q 1/68* (2006.01)
*G01N 33/50* (2006.01)
*C07K 14/47* (2006.01)

(52) U.S. Cl.
CPC ..... *G01N 33/5041* (2013.01); *C07K 14/4722* (2013.01); *C12Q 1/6897* (2013.01); *C07K 2319/00* (2013.01); *C12Q 2600/136* (2013.01); *C12Q 2600/158* (2013.01); *G01N 2333/726* (2013.01); *G01N 2500/04* (2013.01); *G01N 2500/10* (2013.01)

(58) Field of Classification Search
None
See application file for complete search history.

(56) References Cited

U.S. PATENT DOCUMENTS

2008/0280303 A1    11/2008    Burstein et al.
2010/0167397 A1    7/2010    Sasaki et al.

OTHER PUBLICATIONS

Brown et al., Yeast, vol. 16 (2000) pp. 11-22.*
International Search Report and Written Opinion for Application No. PCT/US2012/071412, dated Apr. 10, 2013 (13 pages).
NCBI, GeneBank accession No. CAA30084.1, Sep. 12, 1993.
Zaman et al., "Cryopreserved cells facilitate cell-based drug discovery," *Drug Discovery Today*, 12(13/14): 521-526, (2007).
Conklin et al., "Substitution of three amino acids switches receptor specificity of $G_q\alpha$ to that of $G_i\alpha$," *Nature* 363:274-276, 1993.
Conklin et al., "Carboxyl-Terminal Mutations of $G_{q\alpha}$ and $G_{s\alpha}$ That Alter the Fidelity of Receptor Activation," *Molecular Pharmacology* 50:885-890, 1996.
Durocher et al., "A Reporter Gene Assay for High-Throughput Screening of G-Protein-Coupled Receptors Stably or Transiently Expressed in HEK293 EBNA Cells Grown in Suspension Culture" *Analytical Biochemistry* 284:316-326, 2000.
Milligan et al., "Chimaeric $G_\alpha$ proteins: their potential use in drug discovery," *Pharmacol Sci* 20:118-124, 1999.
Offermanns et al., "$G\alpha_{15}$ and $G\alpha_{16}$ Couple a Wide Variety of Receptors to Phospholipase C*," *The Journal of Biological Chemistry* 270(25):15175-15180, 1995.

* cited by examiner

*Primary Examiner* — Jim Ketter
(74) *Attorney, Agent, or Firm* — Seed IP Law Group LLP

(57) ABSTRACT

Abstract of the Disclosure Disclosed herein are methods and compounds for screening and identifying ligands of G protein-coupled receptors (GPCRs). Also disclosed are chimeric G proteins and methods for detecting the activation or inhibition of GPCRs.

20 Claims, 7 Drawing Sheets

SEQUENCE LISTING

<160> NUMBER OF SEQ ID NOS: 8

<210> SEQ ID NO 1
<211> LENGTH: 394
<212> TYPE: PRT
<213> ORGANISM: Rattus rattus

<400> SEQUENCE: 1

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
            20                  25                  30

Asp Lys Gln Val Tyr Arg Ala Thr His Arg Leu Leu Leu Leu Gly Ala
        35                  40                  45

Gly Glu Ser Gly Lys Ser Thr Ile Val Lys Gln Met Arg Ile Leu His
    50                  55                  60

Val Asn Gly Phe Asn Gly Glu Gly Gly Glu Asp Val Pro Asp Tyr
65                  70                  75                  80

Ala Ser Asn Ser Asp Gly Glu Lys Ala Thr Lys Val Gln Asp Ile Lys
            85                  90                  95

Asn Asn Leu Lys Glu Ala Ile Glu Thr Ile Val Ala Ala Met Ser Asn
        100                 105                 110

Leu Val Pro Pro Val Glu Leu Ala Asn Pro Glu Asn Gln Phe Arg Val
        115                 120                 125

Asp Tyr Ile Leu Ser Val Met Asn Val Pro Asn Phe Asp Phe Pro Pro
        130                 135                 140

Glu Phe Tyr Glu His Ala Lys Ala Leu Trp Glu Asp Glu Gly Val Arg
145                 150                 155                 160

Ala Cys Tyr Glu Arg Ser Asn Glu Tyr Gln Leu Ile Asp Cys Ala Gln
            165                 170                 175

Tyr Phe Leu Asp Lys Ile Asp Val Ile Lys Gln Ala Asp Tyr Val Pro
        180                 185                 190

Ser Asp Gln Asp Leu Leu Arg Cys Arg Val Leu Thr Ser Gly Ile Phe
        195                 200                 205

Glu Thr Lys Phe Gln Val Asp Lys Val Asn Phe His Met Phe Asp Val
        210                 215                 220

Gly Gly Gln Arg Asp Glu Arg Arg Lys Trp Ile Gln Cys Phe Asn Asp
225                 230                 235                 240

Val Thr Ala Ile Ile Phe Val Val Ala Ser Ser Ser Tyr Asn Met Val
            245                 250                 255

Ile Arg Glu Asp Asn Gln Thr Asn Arg Leu Gln Glu Ala Leu Asn Leu
        260                 265                 270

Phe Lys Ser Ile Trp Asn Asn Arg Trp Leu Arg Thr Ile Ser Val Ile
        275                 280                 285

Leu Phe Leu Asn Lys Gln Asp Leu Leu Ala Glu Lys Val Leu Ala Gly
        290                 295                 300

Lys Ser Lys Ile Glu Asp Tyr Phe Pro Glu Phe Ala Arg Tyr Thr Thr
305                 310                 315                 320

Pro Glu Asp Ala Thr Pro Glu Pro Gly Glu Asp Pro Arg Val Thr Arg
            325                 330                 335

Ala Lys Tyr Phe Ile Arg Asp Glu Phe Leu Arg Ile Ser Thr Ala Ser
        340                 345                 350

Gly Asp Gly Arg His Tyr Cys Tyr Pro His Phe Thr Cys Ala Val Asp
        355                 360                 365

Thr Glu Asn Ile Arg Arg Val Phe Asn Asp Cys Arg Asp Ile Ile Gln
370                 375                 380

Arg Met His Leu Arg Gln Tyr Glu Leu Leu
385                 390

<210> SEQ ID NO 2
<211> LENGTH: 394
<212> TYPE: PRT
<213> ORGANISM: Artificial Sequence
<220> FEATURE:
<223> OTHER INFORMATION: Chimeric protein

<400> SEQUENCE: 2

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
                20                  25                  30

Asp Lys Gln Val Tyr Arg Ala Thr His Arg Leu Leu Leu Leu Gly Ala
            35                  40                  45

Gly Glu Ser Gly Lys Ser Thr Ile Val Lys Gln Met Arg Ile Leu His
        50                  55                  60

Val Asn Gly Phe Asn Gly Glu Gly Gly Glu Asp Val Pro Asp Tyr
65                  70                  75                  80

Ala Ser Asn Ser Asp Gly Glu Lys Ala Thr Lys Val Gln Asp Ile Lys
                85                  90                  95

Asn Asn Leu Lys Glu Ala Ile Glu Thr Ile Val Ala Ala Met Ser Asn
            100                 105                 110

Leu Val Pro Pro Val Glu Leu Ala Asn Pro Glu Asn Gln Phe Arg Val
        115                 120                 125

Asp Tyr Ile Leu Ser Val Met Asn Val Pro Asn Phe Asp Phe Pro Pro
    130                 135                 140

Glu Phe Tyr Glu His Ala Lys Ala Leu Trp Glu Asp Glu Gly Val Arg
145                 150                 155                 160

Ala Cys Tyr Glu Arg Ser Asn Glu Tyr Gln Leu Ile Asp Cys Ala Gln
                165                 170                 175

Tyr Phe Leu Asp Lys Ile Asp Val Ile Lys Gln Ala Asp Tyr Val Pro
            180                 185                 190

Ser Asp Gln Asp Leu Leu Arg Cys Arg Val Leu Thr Ser Gly Ile Phe
        195                 200                 205

Glu Thr Lys Phe Gln Val Asp Lys Val Asn Phe His Met Phe Asp Val
    210                 215                 220

Gly Gly Gln Arg Asp Glu Arg Arg Lys Trp Ile Gln Cys Phe Asn Asp
225                 230                 235                 240

Val Thr Ala Ile Ile Phe Val Val Ala Ser Ser Ser Tyr Asn Met Val
                245                 250                 255

Ile Arg Glu Asp Asn Gln Thr Asn Arg Leu Gln Glu Ala Leu Asn Leu
            260                 265                 270

Phe Lys Ser Ile Trp Asn Asn Arg Trp Leu Arg Thr Ile Ser Val Ile
        275                 280                 285

Leu Phe Leu Asn Lys Gln Asp Leu Leu Ala Glu Lys Val Leu Ala Gly
    290                 295                 300

Lys Ser Lys Ile Glu Asp Tyr Phe Pro Glu Phe Ala Arg Tyr Thr Thr
305                 310                 315                 320

Pro Glu Asp Ala Thr Pro Glu Pro Gly Glu Asp Pro Arg Val Thr Arg
                325                 330                 335

```
Ala Lys Tyr Phe Ile Arg Asp Glu Phe Leu Arg Ile Ser Thr Ala Ser
            340                 345                 350

Gly Asp Gly Arg His Tyr Cys Tyr Pro His Phe Thr Cys Ala Val Asp
            355                 360                 365

Thr Glu Asn Ile Arg Arg Val Phe Asn Asp Cys Arg Asp Ile Ile Gln
370                 375                 380

Arg Met His Leu Arg Glu Cys Gly Leu Tyr
385                 390
```

```
<210> SEQ ID NO 3
<211> LENGTH: 394
<212> TYPE: PRT
<213> ORGANISM: Artificial Sequence
<220> FEATURE:
<223> OTHER INFORMATION: Chimeric protein

<400> SEQUENCE: 3
```

```
Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
            20                  25                  30

Asp Lys Gln Val Tyr Arg Ala Thr His Arg Leu Leu Leu Leu Gly Ala
            35                  40                  45

Gly Glu Ser Gly Lys Ser Thr Ile Val Lys Gln Met Arg Ile Leu His
        50                  55                  60

Val Asn Gly Phe Asn Gly Glu Gly Gly Glu Glu Asp Val Pro Asp Tyr
65                  70                  75                  80

Ala Ser Asn Ser Asp Gly Glu Lys Ala Thr Lys Val Gln Asp Ile Lys
                85                  90                  95

Asn Asn Leu Lys Glu Ala Ile Glu Thr Ile Val Ala Ala Met Ser Asn
            100                 105                 110

Leu Val Pro Pro Val Glu Leu Ala Asn Pro Glu Asn Gln Phe Arg Val
            115                 120                 125

Asp Tyr Ile Leu Ser Val Met Asn Val Pro Asn Phe Asp Phe Pro Pro
        130                 135                 140

Glu Phe Tyr Glu His Ala Lys Ala Leu Trp Glu Asp Glu Gly Val Arg
145                 150                 155                 160

Ala Cys Tyr Glu Arg Ser Asn Glu Tyr Gln Leu Ile Asp Cys Ala Gln
                165                 170                 175

Tyr Phe Leu Asp Lys Ile Asp Val Ile Lys Gln Ala Asp Tyr Val Pro
            180                 185                 190

Ser Asp Gln Asp Leu Leu Arg Cys Arg Val Leu Thr Ser Gly Ile Phe
            195                 200                 205

Glu Thr Lys Phe Gln Val Asp Lys Val Asn Phe His Met Phe Asp Val
        210                 215                 220

Gly Gly Gln Arg Asp Glu Arg Arg Lys Trp Ile Gln Cys Phe Asn Asp
225                 230                 235                 240

Val Thr Ala Ile Ile Phe Val Val Ala Ser Ser Tyr Asn Met Val
                245                 250                 255

Ile Arg Glu Asp Asn Gln Thr Asn Arg Leu Gln Glu Ala Leu Asn Leu
            260                 265                 270

Phe Lys Ser Ile Trp Asn Asn Arg Trp Leu Arg Thr Ile Ser Val Ile
            275                 280                 285

Leu Phe Leu Asn Lys Gln Asp Leu Leu Ala Glu Lys Val Leu Ala Gly
        290                 295                 300
```

```
Lys Ser Lys Ile Glu Asp Tyr Phe Pro Glu Phe Ala Arg Tyr Thr Thr
305                 310                 315                 320

Pro Glu Asp Ala Thr Pro Glu Pro Gly Glu Asp Pro Arg Val Thr Arg
                325                 330                 335

Ala Lys Tyr Phe Ile Arg Asp Glu Phe Leu Arg Ile Ser Thr Ala Ser
                340                 345                 350

Gly Asp Gly Arg His Tyr Cys Tyr Pro His Phe Thr Cys Ala Val Asp
                355                 360                 365

Thr Glu Asn Ile Arg Arg Val Phe Asn Asp Cys Arg Asp Ile Ile Ile
            370                 375                 380

Lys Glu Asn Leu Lys Asp Cys Gly Leu Phe
385                 390

<210> SEQ ID NO 4
<211> LENGTH: 394
<212> TYPE: PRT
<213> ORGANISM: Artificial Sequence
<220> FEATURE:
<223> OTHER INFORMATION: Chimeric protein

<400> SEQUENCE: 4

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
                20                  25                  30

Asp Lys Gln Val Tyr Arg Ala Thr His Arg Leu Leu Leu Leu Gly Ala
                35                  40                  45

Gly Glu Ser Gly Lys Ser Thr Ile Val Lys Gln Met Arg Ile Leu His
            50                  55                  60

Val Asn Gly Phe Asn Gly Glu Gly Gly Glu Asp Val Pro Asp Tyr
65                  70                  75                  80

Ala Ser Asn Ser Asp Gly Glu Lys Ala Thr Lys Val Gln Asp Ile Lys
                85                  90                  95

Asn Asn Leu Lys Glu Ala Ile Glu Thr Ile Val Ala Ala Met Ser Asn
            100                 105                 110

Leu Val Pro Pro Val Glu Leu Ala Asn Pro Glu Asn Gln Phe Arg Val
            115                 120                 125

Asp Tyr Ile Leu Ser Val Met Asn Val Pro Asn Phe Asp Phe Pro Pro
            130                 135                 140

Glu Phe Tyr Glu His Ala Lys Ala Leu Trp Glu Asp Glu Gly Val Arg
145                 150                 155                 160

Ala Cys Tyr Glu Arg Ser Asn Glu Tyr Gln Leu Ile Asp Cys Ala Gln
                165                 170                 175

Tyr Phe Leu Asp Lys Ile Asp Val Ile Lys Gln Ala Asp Tyr Val Pro
                180                 185                 190

Ser Asp Gln Asp Leu Leu Arg Cys Arg Val Leu Thr Ser Gly Ile Phe
            195                 200                 205

Glu Thr Lys Phe Gln Val Asp Lys Val Asn Phe His Met Phe Asp Val
            210                 215                 220

Gly Gly Gln Arg Asp Glu Arg Arg Lys Trp Ile Gln Cys Phe Asn Asp
225                 230                 235                 240

Val Thr Ala Ile Ile Phe Val Val Ala Ser Ser Ser Tyr Asn Met Val
                245                 250                 255

Ile Arg Glu Asp Asn Gln Thr Asn Arg Leu Gln Glu Ala Leu Asn Leu
                260                 265                 270
```

```
Phe Lys Ser Ile Trp Asn Asn Arg Trp Leu Arg Thr Ile Ser Val Ile
            275                 280                 285

Leu Phe Leu Asn Lys Gln Asp Leu Leu Ala Glu Lys Val Leu Ala Gly
    290                 295                 300

Lys Ser Lys Ile Glu Asp Tyr Phe Pro Glu Phe Ala Arg Tyr Thr Thr
305                 310                 315                 320

Pro Glu Asp Ala Thr Pro Glu Pro Gly Glu Asp Pro Arg Val Thr Arg
                325                 330                 335

Ala Lys Tyr Phe Ile Arg Asp Glu Phe Leu Arg Ile Ser Thr Ala Ser
                340                 345                 350

Gly Asp Gly Arg His Tyr Cys Tyr Pro His Phe Thr Cys Ala Val Asp
            355                 360                 365

Thr Glu Asn Ile Arg Arg Val Phe Asn Asp Cys Arg Asp Ile Ile Ile
    370                 375                 380

Ala Asn Asn Leu Arg Gly Cys Gly Leu Tyr
385                 390

<210> SEQ ID NO 5
<211> LENGTH: 394
<212> TYPE: PRT
<213> ORGANISM: Artificial Sequence
<220> FEATURE:
<223> OTHER INFORMATION: Chimeric protein

<400> SEQUENCE: 5

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
                20                  25                  30

Asp Lys Gln Val Tyr Arg Ala Thr His Arg Leu Leu Leu Leu Gly Ala
            35                  40                  45

Gly Glu Ser Gly Lys Ser Thr Ile Val Lys Gln Met Arg Ile Leu His
        50                  55                  60

Val Asn Gly Phe Asn Gly Glu Gly Gly Glu Glu Asp Val Pro Asp Tyr
65                  70                  75                  80

Ala Ser Asn Ser Asp Gly Glu Lys Ala Thr Lys Val Gln Asp Ile Lys
                85                  90                  95

Asn Asn Leu Lys Glu Ala Ile Glu Thr Ile Val Ala Ala Met Ser Asn
            100                 105                 110

Leu Val Pro Pro Val Glu Leu Ala Asn Pro Glu Asn Gln Phe Arg Val
        115                 120                 125

Asp Tyr Ile Leu Ser Val Met Asn Val Pro Asn Phe Asp Phe Pro Pro
    130                 135                 140

Glu Phe Tyr Glu His Ala Lys Ala Leu Trp Glu Asp Glu Gly Val Arg
145                 150                 155                 160

Ala Cys Tyr Glu Arg Ser Asn Glu Tyr Gln Leu Ile Asp Cys Ala Gln
                165                 170                 175

Tyr Phe Leu Asp Lys Ile Asp Val Ile Lys Gln Ala Asp Tyr Val Pro
            180                 185                 190

Ser Asp Gln Asp Leu Leu Arg Cys Arg Val Leu Thr Ser Gly Ile Phe
        195                 200                 205

Glu Thr Lys Phe Gln Val Asp Lys Val Asn Phe His Met Phe Asp Val
    210                 215                 220

Gly Gly Gln Arg Asp Glu Arg Arg Lys Trp Ile Gln Cys Phe Asn Asp
225                 230                 235                 240
```

```
Val Thr Ala Ile Ile Phe Val Val Ala Ser Ser Tyr Asn Met Val
            245                 250                 255

Ile Arg Glu Asp Asn Gln Thr Asn Arg Leu Gln Glu Ala Leu Asn Leu
        260                 265                 270

Phe Lys Ser Ile Trp Asn Asn Arg Trp Leu Arg Thr Ile Ser Val Ile
        275                 280                 285

Leu Phe Leu Asn Lys Gln Asp Leu Leu Ala Glu Lys Val Leu Ala Gly
        290                 295                 300

Lys Ser Lys Ile Glu Asp Tyr Phe Pro Glu Phe Ala Arg Tyr Thr Thr
305                 310                 315                 320

Pro Glu Asp Ala Thr Pro Glu Pro Gly Glu Asp Pro Arg Val Thr Arg
                325                 330                 335

Ala Lys Tyr Phe Ile Arg Asp Glu Phe Leu Arg Ile Ser Thr Ala Ser
                340                 345                 350

Gly Asp Gly Arg His Tyr Cys Tyr Pro His Phe Thr Cys Ala Val Asp
            355                 360                 365

Thr Glu Asn Ile Arg Arg Val Phe Asn Asp Cys Arg Asp Val Ile Ile
        370                 375                 380

Lys Asn Asn Leu Lys Asp Cys Gly Leu Phe
385                 390

<210> SEQ ID NO 6
<211> LENGTH: 394
<212> TYPE: PRT
<213> ORGANISM: Artificial Sequence
<220> FEATURE:
<223> OTHER INFORMATION: Chimeric protein

<400> SEQUENCE: 6

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
                20                  25                  30

Asp Lys Gln Val Tyr Arg Ala Thr His Arg Leu Leu Leu Leu Gly Ala
            35                  40                  45

Gly Glu Ser Gly Lys Ser Thr Ile Val Lys Gln Met Arg Ile Leu His
        50                  55                  60

Val Asn Gly Phe Asn Gly Glu Gly Gly Glu Glu Asp Val Pro Asp Tyr
65                  70                  75                  80

Ala Ser Asn Ser Asp Gly Glu Lys Ala Thr Lys Val Gln Asp Ile Lys
                85                  90                  95

Asn Asn Leu Lys Glu Ala Ile Glu Thr Ile Val Ala Ala Met Ser Asn
            100                 105                 110

Leu Val Pro Pro Val Glu Leu Ala Asn Pro Glu Asn Gln Phe Arg Val
        115                 120                 125

Asp Tyr Ile Leu Ser Val Met Asn Val Pro Asn Phe Asp Phe Pro Pro
    130                 135                 140

Glu Phe Tyr Glu His Ala Lys Ala Leu Trp Glu Asp Glu Gly Val Arg
145                 150                 155                 160

Ala Cys Tyr Glu Arg Ser Asn Glu Tyr Gln Leu Ile Asp Cys Ala Gln
                165                 170                 175

Tyr Phe Leu Asp Lys Ile Asp Val Ile Lys Gln Ala Asp Tyr Val Pro
            180                 185                 190

Ser Asp Gln Asp Leu Leu Arg Cys Arg Val Leu Thr Ser Gly Ile Phe
        195                 200                 205
```

```
Glu Thr Lys Phe Gln Val Asp Lys Val Asn Phe His Met Phe Asp Val
    210                 215                 220
Gly Gly Gln Arg Asp Glu Arg Arg Lys Trp Ile Gln Cys Phe Asn Asp
225                 230                 235                 240
Val Thr Ala Ile Ile Phe Val Val Ala Ser Ser Ser Tyr Asn Met Val
                245                 250                 255
Ile Arg Glu Asp Asn Gln Thr Asn Arg Leu Gln Glu Ala Leu Asn Leu
                260                 265                 270
Phe Lys Ser Ile Trp Asn Asn Arg Trp Leu Arg Thr Ile Ser Val Ile
                275                 280                 285
Leu Phe Leu Asn Lys Gln Asp Leu Leu Ala Glu Lys Val Leu Ala Gly
    290                 295                 300
Lys Ser Lys Ile Glu Asp Tyr Phe Pro Glu Phe Ala Arg Tyr Thr Thr
305                 310                 315                 320
Pro Glu Asp Ala Thr Pro Glu Pro Gly Glu Asp Pro Arg Val Thr Arg
                325                 330                 335
Ala Lys Tyr Phe Ile Arg Asp Glu Phe Leu Arg Ile Ser Thr Ala Ser
                340                 345                 350
Gly Asp Gly Arg His Tyr Cys Tyr Pro His Phe Thr Cys Ala Val Asp
                355                 360                 365
Thr Glu Asn Ile Arg Arg Val Phe Asn Asp Cys Arg Asp Val Ile Ile
    370                 375                 380
Gln Asn Asn Leu Lys Tyr Ile Gly Leu Cys
385                 390
```

<210> SEQ ID NO 7
<211> LENGTH: 394
<212> TYPE: PRT
<213> ORGANISM: Artificial Sequence
<220> FEATURE:
<223> OTHER INFORMATION: Chimeric protein

<400> SEQUENCE: 7

```
Met Gly Cys Leu Gly Asn Ser Lys Thr Glu Asp Gln Arg Asn Glu Glu
1               5                   10                  15
Lys Ala Gln Arg Glu Ala Asn Lys Lys Ile Glu Lys Gln Leu Gln Lys
                20                  25                  30
Asp Lys Gln Val Tyr Arg Ala Thr His Arg Leu Leu Leu Leu Gly Ala
                35                  40                  45
Gly Glu Ser Gly Lys Ser Thr Ile Val Lys Gln Met Arg Ile Leu His
    50                  55                  60
Val Asn Gly Phe Asn Gly Glu Gly Gly Glu Asp Val Pro Asp Tyr
65                  70                  75                  80
Ala Ser Asn Ser Asp Gly Glu Lys Ala Thr Lys Val Gln Asp Ile Lys
                85                  90                  95
Asn Asn Leu Lys Glu Ala Ile Glu Thr Ile Val Ala Ala Met Ser Asn
                100                 105                 110
Leu Val Pro Pro Val Glu Leu Ala Asn Pro Glu Asn Gln Phe Arg Val
                115                 120                 125
Asp Tyr Ile Leu Ser Val Met Asn Val Pro Asn Phe Asp Phe Pro Pro
                130                 135                 140
Glu Phe Tyr Glu His Ala Lys Ala Leu Trp Glu Asp Glu Gly Val Arg
145                 150                 155                 160
Ala Cys Tyr Glu Arg Ser Asn Glu Tyr Gln Leu Ile Asp Cys Ala Gln
                165                 170                 175
```

```
Tyr Phe Leu Asp Lys Ile Asp Val Ile Lys Gln Ala Asp Tyr Val Pro
            180                 185                 190

Ser Asp Gln Asp Leu Leu Arg Cys Arg Val Leu Thr Ser Gly Ile Phe
        195                 200                 205

Glu Thr Lys Phe Gln Val Asp Lys Val Asn Phe His Met Phe Asp Val
    210                 215                 220

Gly Gly Gln Arg Asp Glu Arg Arg Lys Trp Ile Gln Cys Phe Asn Asp
225                 230                 235                 240

Val Thr Ala Ile Ile Phe Val Val Ala Ser Ser Tyr Asn Met Val
                245                 250                 255

Ile Arg Glu Asp Asn Gln Thr Asn Arg Leu Gln Glu Ala Leu Asn Leu
            260                 265                 270

Phe Lys Ser Ile Trp Asn Asn Arg Trp Leu Arg Thr Ile Ser Val Ile
        275                 280                 285

Leu Phe Leu Asn Lys Gln Asp Leu Leu Ala Glu Lys Val Leu Ala Gly
    290                 295                 300

Lys Ser Lys Ile Glu Asp Tyr Phe Pro Glu Phe Ala Arg Tyr Thr Thr
305                 310                 315                 320

Pro Glu Asp Ala Thr Pro Glu Pro Gly Glu Asp Pro Arg Val Thr Arg
                325                 330                 335

Ala Lys Tyr Phe Ile Arg Asp Glu Phe Leu Arg Ile Ser Thr Ala Ser
            340                 345                 350

Gly Asp Gly Arg His Tyr Cys Tyr Pro His Phe Thr Cys Ala Val Asp
        355                 360                 365

Thr Glu Asn Ile Arg Arg Val Phe Asn Asp Cys Arg Asp Ser Val Leu
    370                 375                 380

Ala Arg Tyr Leu Asp Glu Ile Asn Leu Leu
385                 390

<210> SEQ ID NO 8
<211> LENGTH: 394
<212> TYPE: PRT
<213> ORGANISM: Artificial Sequence
<220> FEATURE:
<223> OTHER INFORMATION: Chimeric protein

<400> SEQUENCE: 8

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
            20                  25                  30

Asp Lys Gln Val Tyr Arg Ala Thr His Arg Leu Leu Leu Leu Gly Ala
        35                  40                  45

Gly Glu Ser Gly Lys Ser Thr Ile Val Lys Gln Met Arg Ile Leu His
    50                  55                  60

Val Asn Gly Phe Asn Gly Glu Gly Gly Glu Asp Val Pro Asp Tyr
65                  70                  75                  80

Ala Ser Asn Ser Asp Gly Glu Lys Ala Thr Lys Val Gln Asp Ile Lys
                85                  90                  95

Asn Asn Leu Lys Glu Ala Ile Glu Thr Ile Val Ala Ala Met Ser Asn
            100                 105                 110

Leu Val Pro Pro Val Glu Leu Ala Asn Pro Glu Asn Gln Phe Arg Val
        115                 120                 125

Asp Tyr Ile Leu Ser Val Met Asn Val Pro Asn Phe Asp Phe Pro Pro
    130                 135                 140
```

-continued

```
Glu Phe Tyr Glu His Ala Lys Ala Leu Trp Glu Asp Glu Gly Val Arg
145                 150                 155                 160

Ala Cys Tyr Glu Arg Ser Asn Glu Tyr Gln Leu Ile Asp Cys Ala Gln
                165                 170                 175

Tyr Phe Leu Asp Lys Ile Asp Val Ile Lys Gln Ala Asp Tyr Val Pro
            180                 185                 190

Ser Asp Gln Asp Leu Leu Arg Cys Arg Val Leu Thr Ser Gly Ile Phe
        195                 200                 205

Glu Thr Lys Phe Gln Val Asp Lys Val Asn Phe His Met Phe Asp Val
    210                 215                 220

Gly Gly Gln Arg Asp Glu Arg Arg Lys Trp Ile Gln Cys Phe Asn Asp
225                 230                 235                 240

Val Thr Ala Ile Ile Phe Val Val Ala Ser Ser Ser Tyr Asn Met Val
                245                 250                 255

Ile Arg Glu Asp Asn Gln Thr Asn Arg Leu Gln Glu Ala Leu Asn Leu
            260                 265                 270

Phe Lys Ser Ile Trp Asn Asn Arg Trp Leu Arg Thr Ile Ser Val Ile
        275                 280                 285

Leu Phe Leu Asn Lys Gln Asp Leu Leu Ala Glu Lys Val Leu Ala Gly
    290                 295                 300

Lys Ser Lys Ile Glu Asp Tyr Phe Pro Glu Phe Ala Arg Tyr Thr Thr
305                 310                 315                 320

Pro Glu Asp Ala Thr Pro Glu Pro Gly Glu Asp Pro Arg Val Thr Arg
                325                 330                 335

Ala Lys Tyr Phe Ile Arg Asp Glu Phe Leu Arg Ile Ser Thr Ala Ser
            340                 345                 350

Gly Asp Gly Arg His Tyr Cys Tyr Pro His Phe Thr Cys Ala Val Asp
        355                 360                 365

Thr Glu Asn Ile Arg Arg Val Phe Asn Asp Cys Arg Asp Thr Ile Leu
    370                 375                 380

Gln Leu Asn Leu Lys Glu Tyr Asn Leu Val
385                 390
```

METHODS AND G PROTEINS FOR SCREENING AND IDENTIFYING LIGANDS OF G PROTEIN-COUPLED RECEPTORS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360066_403USPC_SEQUENCE_LISTING.txt. The text file is 27.3 KB, was created on Jun. 19, 2014, and is being submitted electronically via EFS-Web.

TECHNICAL FIELD

The invention relates to methods and G proteins for screening and identifying ligands of G protein-coupled receptors (GPCRs). The invention also relates to chimeric G proteins and methods for detecting the activation or inhibition of GPCRs.

BACKGROUND

GPCRs constitute a large and diverse family of proteins that function to transduce extracellular stimuli into intracellular signals. They also represent nearly half of all pharmaceutical drug targets currently on the market today. Many GPCRs act as receptors for a variety of signaling molecules from small molecules to large proteins, including hormones, neurotransmitters, cytokines, and lipids. These proteins also act as receptors for environmental stimuli that are sensed as odors, tastes, pheromones, or light.

The GPCRs are integral membrane proteins that possess seven membrane-spanning helices with an extracellular N-terminus and an intracellular C-terminus. The GPCR is activated by the recognition of a ligand which leads to a conformational change in the receptor. The conformational change in the GPCR leads to the activation of a coupled G protein. Depending on the type of G protein to which the GPCR is coupled, a variety of downstream signaling pathways can be activated.

G proteins include heterotrimeric G proteins comprising three different subunits: the Gα subunit, the Gβ subunit, and the Gγ subunit. GPCRs transduce signals by catalyzing the dissociation of a coupled heterotrimeric G protein into a GTP-bound Gα subunit and a Gβ/Gγ subunit complex, each of which can independently initiate intracellular signaling events. There are many different Gα subunits, including $G\alpha_s$, $G\alpha_t$, $G\alpha_o$, $G\alpha_i$, $G\alpha_z$, $G\alpha_{15}$, $G\alpha_k$, and $G\alpha_q$. The different Gα subunits vary with regard to the GPCR that they may couple with and the signaling pathways they activate.

Several major signal transduction pathways are mediated by different Gα subunits, including stimulation ($G\alpha_s$) or inhibition ($G\alpha_i$) of the effector adenylyl cyclase, and activation of the effector phospholipase C ($G\alpha_q$). Activation of the effector adenylyl cyclase by $G\alpha_s$ results in the modulation of the second messenger cyclic adenosine monophosphate (cAMP), which, in turn, can regulate the functions of protein kinase A and other proteins. The interaction of cAMP with protein kinases then leads to phosphorylation and activation of various transcription factors. Cell-based assays relying on transcriptionally controlled reporter genes could be well suited for high throughput screening and the identification of GPCR ligands. However, because each GPCR generally interacts with only one or a few types of Gα subunits, there is no universal assay that can be used for ligand or drug screening with all GPCRs. Furthermore, existing strategies for screening of GPCRs are sophisticated and expensive.

DETAILED DESCRIPTION

Figure 1A:
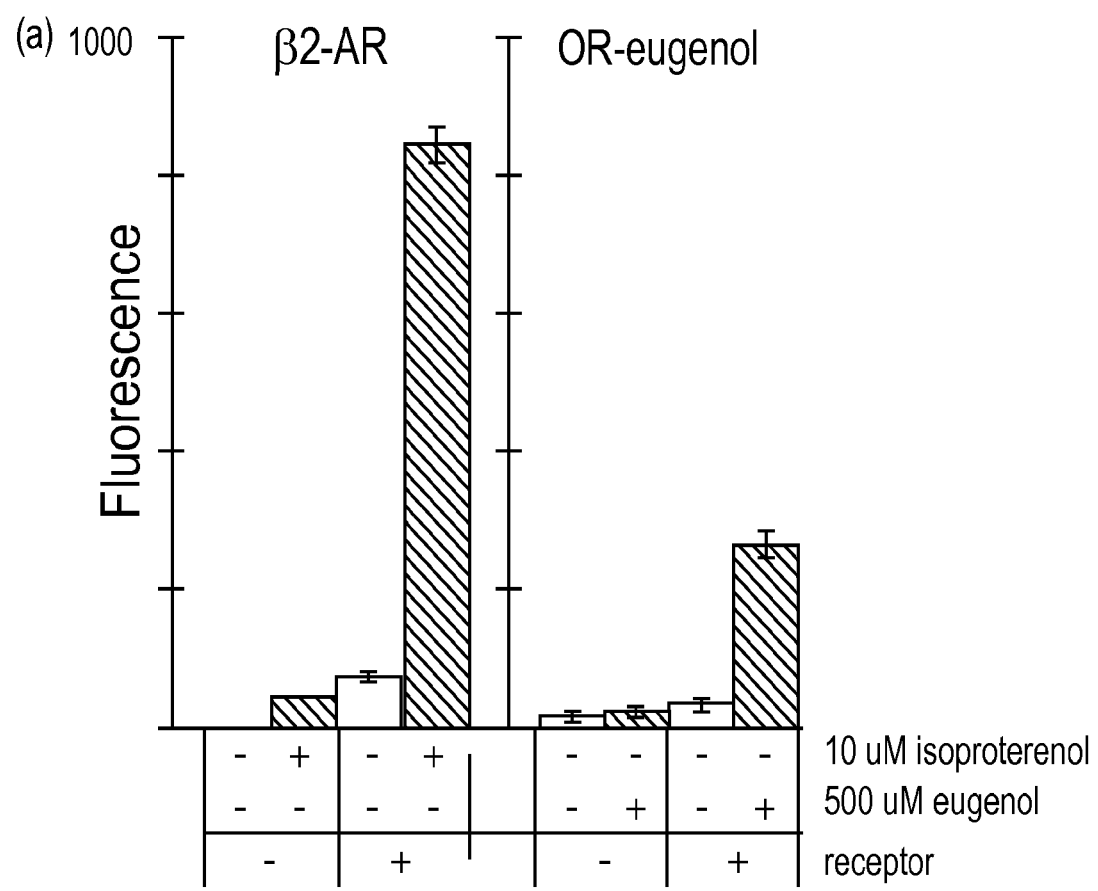
FIG. 1 shows the results of testing for the coupling of the M2 acetylcholine receptor (M2AchR) GPCR to unsubstituted $G\alpha_s$ compared to $G\alpha_s$-based chimeric proteins according to the present description with C-terminal amino acids substituted with the C-terminal amino acids of other Gα subunits.

Disclosed herein are methods for screening and identifying ligands of GPCRs. The methods described herein include methods for identifying GPCR ligands using chimeric G proteins. In certain embodiments, the chimeric G proteins utilized in the methods described herein may be activated by a variety of different GPCRs. The methods described herein may be used to screen for ligands that activate or inhibit GPCRs. In particular embodiments, the methods may include the characterization of orphan GPCRs using a cell-based assay as disclosed herein.

In certain embodiments, the methods described herein include a cell-based assay for screening and identifying GPCR ligands by using a cAMP-dependent reporter gene system, wherein GPCR ligand binding leads to the activation of a $G\alpha_s$-based chimeric G protein that stimulates adenylyl cyclase and thus increases cAMP.

Chimeric G proteins for use in the methods disclosed herein are also provided. The chimeric G proteins described herein comprise a chimeric Gα subunit and in some embodiments, the chimeric G proteins promiscuously couple with a variety of GPCRs and may be used to identify GPCR ligands. In particular embodiments, the chimeric G proteins described herein include a $G\alpha_s$-based chimeric subunit comprising substituted C-terminal amino acids. Oligonucleotides encoding chimeric G proteins that may be used in a cell-based assay for the screening of GPCR ligands are also provided herein. Further, expression vectors comprising DNA constructs for the expression of $G\alpha_s$-based chimeric G proteins and cell lines stably expressing $G\alpha_s$-based chimeric G proteins are disclosed.

I. DEFINITIONS

It is to be understood that the terminology used herein is for the purpose of describing particular embodiments only, and is not intended to limit the scope of the present invention which will be limited only by the appended claims.

Unless defined otherwise, all technical and scientific terms used herein have the meanings that would be commonly understood by one of skill in the art. As used herein, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount.

Unless otherwise indicated, the term "include" has the same meaning as "include, but are not limited to," the term "includes" has the same meaning as "includes, but is not limited to," and the term "including" has the same meaning as "including, but not limited to." Similarly, the term "such as" has the same meaning as the term "such as, but not limited to."

As used herein, the term "ligand" refers to a molecule or compound (e.g. including molecules such as peptides and lipids) that binds to a receptor. Receptor ligands, such as GPCR ligands, are well understood in the art and, for purposes of example only, can be molecules that are receptor agonists, receptor antagonists, receptor activators, and receptor inhibitors. The term "candidate GPCR ligand" refers to a compound or molecule that may be a GPCR ligand and may be screened according to the methods disclosed herein.

The term "reporter gene" refers to a gene whose expression may be monitored to detect various biologic functions such as DNA expression and promoter activity in a cell or tissue. Reporter genes may be part of a DNA construct or expression vector in which the reporter gene is attached to a promoter region and the DNA construct or expression vector may be transfected into a cell.

The terms "activate," "activating," and "activation" refer to an increase in an activity, response, condition, or other biological parameter, including the increased production, presence, expression, or function of cells, biomolecules or bioactive molecules. The terms "activate," "activating," and "activation" include, but are not limited to, the initiation of an activity, response, or condition, as well as the initiation of the production, presence, or expression of cells, biomolecules, or bioactive molecules. The terms "activate," "activating," and "activation" may also include a measurable increase in an activity, response, or condition, or a measurable increase in the production, presence, or expression of cells, biomolecules, or bioactive molecules, as compared to a native or control level.

The terms "inhibit," "inhibiting," and "inhibition" refer to a decrease in an activity, response, condition, or other biological parameter, including the production, presence, expression, or function of cells, biomolecules or bioactive molecules. The terms "inhibit," "inhibiting," and "inhibition" include, but are not limited to, the complete ablation of an activity, response, or condition, as well as the complete ablation of the production, presence, or expression of cells, biomolecules, or bioactive molecules. The terms "inhibit," "inhibiting," and "inhibition" may also include a measurable reduction in an activity, response, or condition, or a measurable reduction in the production, presence, or expression of cells, biomolecules, or bioactive molecules, as compared to a native or control level.

The term "orphan GPCR" refers to GPCRs that act as receptors for ligands that have not yet been identified. As used herein, an orphan GPCR may also be a GPCR that has an unknown G protein coupling preference.

As the terms are used herein, "protein" and "peptide" are used to simply refer to polypeptide molecules generally and are not used to refer to polypeptide molecules of any specific size, length or molecular weight. Protein variants and derivatives are well understood to those of skill in the art and can involve amino acid sequence modifications. Amino acid substitutions may include one or more residues and can occur at a number of different locations at once. Substitutions, deletions, insertions or any combination thereof may be combined to arrive at a final construct.

The term "substituted," when used to describe the amino acid sequence of a protein or polypeptide, refers to a derivative of that amino acid sequence wherein one or more of its amino acids are substituted for another amino acid. As such, proteins or peptides with substituted amino acids are those in which at least one amino acid residue has been removed and a different residue inserted in its place.

For example, the replacement of one amino acid residue with another that is biologically and/or chemically similar is known to those skilled in the art as a conservative substitution. For example, a conservative substitution would be replacing one hydrophobic amino acid residue for another, or one polar amino acid residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the polypeptides provided herein.

Substantial changes in peptide function or immunological identity may be made by selecting amino acid substitutions that differ in their effect on maintaining, for example, (a) the structure of the polypeptide backbone in the area of the substitution, for example as a sheet or helical conformation, (b) allosteric regulation of other regions of the polypeptide, (c) the charge or hydrophobicity of the molecule at the target site or (d) the bulk of the side chain. The substitutions which may produce changes in the protein properties can include those in which (a) a hydrophilic residue, e.g. seryl or threonyl, is substituted for (or by) a hydrophobic residue, e.g. leucyl, isoleucyl, phenylalanyl, valyl or alanyl; (b) a Cys or Pro is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., Phe, is substituted for (or by) one not having a side chain, e.g., Gly, in this case, (e) by increasing the number of sites for sulfation and/or glycosylation.

As this specification discusses various proteins and protein sequences, it is understood that the nucleic acids that can encode those protein sequences are also disclosed. This would include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed compounds. For example, there are numerous D amino acids or amino acids which have a different functional substituent. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber stop codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); and Ibba and Hennecke, Bio/technology, 12:678-682 (1994)).

The terms "oligonucleotide" or "polynucleotide" as used herein refer to a nucleic acid made up of a number of nucleotides. As known by those of skill in the art, a nucleotide is a molecule that contains a base moiety, a sugar moiety and a phosphate moiety. Nucleotides can be linked together through their phosphate moieties and sugar moieties creating an internucleoside linkage. Nucleic acids include DNA and RNA and function in encoding, transmitting and expressing genetic information. For example, a nucleic acid may code for one or more amino acids that may comprise a protein.

The nucleic acids disclosed herein, such as the DNA coding for chimeric G proteins and the oligonucleotides to be used as PCR primers, include nucleotides, nucleotide analogs, or nucleotide substitutes and can be made using standard chemical synthesis methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method).

The nucleic acids disclosed herein can be introduced into expression vectors or cloning vectors by operatively linking the DNA construct to the necessary expression control regions (e.g. regulatory regions) required for DNA expression or into e.g. a multiple cloning site. The vectors can be introduced into the appropriate host cells such as prokaryotic (e.g., bacterial), or eukaryotic (e.g., yeast or mammalian) cells by methods well known in the art.

The term "vector" or "expression vector" refers to a vehicle that is capable of delivering a nucleic acid sequence into a host cell for replication purposes. Vectors are especially designed to provide an environment which allows the expression of the cloned gene after transformation into the host. One manner of providing such an environment is to include transcriptional and translational regulatory sequences on such vectors, such transcriptional and translational regulatory sequences capable of being operably linked to the cloned gene. In a vector, the gene to be cloned is usually operably-linked to certain control sequences such as promoter sequences. Expression control sequences may contain transcriptional elements such as enhancer elements, termination sequences, tissue-specificity elements, and/or translational initiation and termination sites. Numerous vectors are known to those of skill in the art and can be delivered to a cell in a variety of ways. For example, the vectors can be delivered through electroporation, sonoporation, lipofection, or through calcium phosphate precipitation. The delivery mechanism chosen will depend in part on the type of cell targeted. The terms expression vector and vector also encompass naked DNA which may be operably linked to a promoter.

The term "isolated polypeptide" as used herein refers to a polypeptide that is isolated from a source. In one embodiment, the isolated polypeptide may be of a purity selected from approximately at least 1% pure, at least 5% pure, at least 10% pure, at least 20% pure, at least 40% pure, at least 60% pure, at least 80% pure, and at least 90% pure.

The term "isolated oligonucleotide" as used herein refers to an oligonucleotide that is isolated from a source. In one embodiment, the isolated oligonucleotide may be of a purity selected from approximately at least 1% pure, at least 5% pure, at least 10% pure, at least 20% pure, at least 40% pure, at least 60% pure, at least 80% pure, and at least 90% pure.

II. METHODS OF SCREENING AND IDENTIFYING GPCR LIGANDS

Disclosed herein are methods for screening and identifying ligands of GPCRs. Embodiments of the methods described herein include administering a candidate GPCR ligand to a cell expressing a GPCR of interest, and a chimeric G protein as described herein, and determining if the candidate ligand has activated or inhibited the GPCR. In one such embodiment, the methods disclosed herein include an assay for screening and identifying GPCR ligands by using a cell-based cAMP-dependent reporter gene assay, wherein GPCR ligand binding leads to the activation of a chimeric G protein that stimulates adenylyl cyclase, and thus increases cAMP and causes the expression of the reporter gene. In particular embodiments, the methods disclosed herein include a cell-based assay comprising a cell expressing a chimeric G protein that is a $G\alpha_s$-based chimeric G protein, wherein ligand binding leads to activation of the effector adenylyl cyclase by $G\alpha_s$, resulting in an increase in cAMP. Accordingly, the methods disclosed herein include assays that identify GPCR ligand binding by detecting an increase in cAMP, and assays that identify a GPCR ligand by detecting a decrease in cAMP (for example, detecting an antagonist ligand).

The methods disclosed herein may include suitable cAMP-dependent assays or cAMP detection systems known in the art. For example, methods of detecting cAMP include measuring cAMP levels using a competition assay in which cellular cAMP competes with an introduced, labeled form of cAMP for binding to an anti-cAMP antibody. Other methods for detecting cAMP levels include radiometric assays such as scintillation proximity assays (SPA, Amersham) and Flashplate (Perkin Elmer) using I-125-labeled cAMP, fluorescence polarization, homogenous time-resolved fluorescence (HTRF, Cisbio). Other methods for detecting cAMP levels include the use of fusion proteins containing cAMP-binding domains (derived from PKA or other protein) and reporter fluorophores and enzymes, including GFP, luciferase, and phosphatase (for example, the GloSensor kit from Promega). The cAMP-dependent assays for use in the methods described herein are advantageous because they facilitate early and direct characterization of potential GPCR ligands and can be relatively inexpensive and scalable for high throughput screening.

In one embodiment, the methods disclosed herein include a cAMP detection system such as a cAMP-dependent reporter gene assay that may be the CRE-SEAP reporter gene assay, as discussed in Durocher et al., Anal Biochem 284: 316-326 (2000), incorporated herein by reference. The CRE-SEAP assay is a high throughput assay that is based on the activation of adenyl cyclase by a $G\alpha_s$-coupled GPCR. The CRE-SEAP assay comprises the use of a CRE-SEAP plasmid, pCRE-SEAP (BD Biosciences Clontech). The pCRE-SEAP includes DNA coding for the secreted form of the human placental alkaline phosphatase (SEAP) under the control of the vasoactive intestinal peptide (VIP) promoter containing a total of five cyclic AMP response elements (GREs). Accordingly, the activation of a $G\alpha_s$-coupled GPCR leads to an increase in cAMP and, in a cell transfected with the pCRE-SEAP, promotes the expression of the reporter gene SEAP under control of CRE. The SEAP levels may be detected using any suitable technique and method including, for example, fluorescence, chemiluminescence, radiolabeling, immunoassay, enzymes, and the like. Other CRE reporter genes that drive expression of luciferase, fluorescent proteins, or other reporter enzymes could also be used.

A consideration for use of the methods and chimeric G proteins disclosed herein is that there are many GPCRs that do not normally couple to $G\alpha_s$. A high throughput cAMP-dependent reporter gene construct, such as CRE-SEAP, cannot generally be used with those GPCRs that do not couple to $G\alpha_s$. Previous studies have used $G\alpha_{15}$, a G protein of the $G\alpha_q$ class that couples to a variety of GPCRs (Offermanns S and Simon M I, C. J Biol Chem 270: 15175-15180 (1995)). Additionally, chimeric G proteins have been used in which a C-terminal portion of $G\alpha_q$ has been replaced by the corresponding portion of other $G\alpha$ subunits (Milligan G and Rees S, Trends Pharmacol Sci 20: 118-124 (1999); Conklin et al., Nature 363: 274-276 (1993); and Conklin et al., Mol Pharmacol 50: 885-890 (1996)). However, such methods are complex, relatively expensive, and often do not work with many GPCRs. Furthermore, for both of the referenced strategies, the activated $G\alpha_q$ subunit G protein stimulates phospholipase C, and not cAMP, and is therefore not suitable for a cAMP-dependent assay. Therefore, the screening methods described herein, which utilize $G\alpha_s$-based chimeric G proteins as described herein, can facilitate the use of a cAMP-dependent high throughput assay for the screening and identification of GPCR ligands. In the embodiments described herein, the chimeric G proteins exhibit promiscuous coupling with two or more different GPCRs and the methods themselves can be relatively easily and inexpensively adapted for high throughput screening of ligands capable of activating or inhibiting a variety of different GPCRs.

In particular embodiments, the methods disclosed herein include a cell-based assay for screening and identifying GPCR ligands by using a cell comprising a cAMP detection system and a $G\alpha_s$-based chimeric G protein which promiscuously couples to a variety of GPCRs. In one such embodiment, the method comprises a cell-based assay with a cell line cotransfected with (i) a GPCR of interest, (ii) a $G\alpha_s$-based chimeric G protein as described herein, and (iii) a cAMP detection system, wherein GPCR ligand binding leads to the activation of the $G\alpha_s$-based chimeric G protein, thereby increasing cAMP and promoting expression of the reporter gene. The $G\alpha_s$-based chimeric G proteins disclosed herein may comprise the substitution of the C-terminal amino acids of a $G\alpha_s$ subunit, such as a rat $G\alpha_s$ subunit (SEQ ID NO: 1), with the C-terminal amino acids of a different $G\alpha$ subunit. The substitution of the C-terminal amino acids of $G\alpha_s$ with the C-terminal amino acids of a different $G\alpha$ subunit allow the $G\alpha_s$-based chimera to promiscuously couple with GPCRs that would not normally couple with $G\alpha_s$. As such, the methods disclosed herein comprising a cell-based cAMP detection system, including $G\alpha_s$-based chimeric proteins, will allow for the screening of a large variety of GPCRs that could not normally be screened with a cAMP-dependent assay.

In examples of the methods disclosed herein, the chimeric G protein utilized for screening may be characterized by one or more of the C-terminal amino acids of a $G\alpha_s$ subunit substituted with one or more of the C-terminal amino acids from a different $G\alpha$ subunit, such as a $G\alpha_o$ subunit, a $G\alpha_z$ subunit, a $G\alpha_t$ subunit, a $G\alpha_q$ subunit, a $G\alpha_{15}$ subunit, a $G\alpha_o$ subunit, or a $G\alpha_k$ subunit. In one such example, the C-terminal amino acids of a $G\alpha_s$ subunit used in the chimeric G protein may be substituted with at least 1, 2, 3, 4, 5, 6, 7, 8, 9, 10, 11, 12, 13, 14, 15, 16, 17, 18, 19, and 20, or more, amino acids from a $G\alpha_o$ subunit, a $G\alpha_z$ subunit, a $G\alpha_t$ subunit, a $G\alpha_q$ subunit, a $G\alpha_{15}$ subunit, a $G\alpha_o$ subunit, or a $G\alpha_k$ subunit. In certain such examples, the C-terminal amino acid substitutions include an amino acid substitution of about 2-5, 2-10, 2-13, 2-15, 5-10, 5-15, 5-20, 10-15, and 10-20 of the C-terminal amino acids of the $G\alpha_s$ subunit. In particular examples, the chimeric G protein used in the methods described herein may include a $G\alpha_s$-based chimeric G protein selected from $G\alpha_s$-$G\alpha_k$-5 (SEQ ID NO: 2), $G\alpha_s$-$G\alpha_t$-13 (SEQ ID NO: 3), $G\alpha_s$-$G\alpha_o$-13 (SEQ ID NO: 4), $G\alpha_s$-$G\alpha_i$-13 (SEQ ID NO: 5), $G\alpha_s$-$G\alpha_z$-13 (SEQ ID NO: 6), $G\alpha_s$-$G\alpha_{15}$-13 (SEQ ID NO: 7), and $G\alpha_s$-$G\alpha_q$-13 (SEQ ID NO: 8).

In examples of the methods disclosed herein, a cell comprising a GPCR of interest, a chimeric G protein as disclosed herein, and a cAMP detection system, such as a cAMP-dependent reporter gene, may be used to screen for GPCR ligands, wherein the method comprises administering a GPCR candidate ligand to the cell and wherein a measurable increase in expression of the reporter gene by the cell indicates the GPCR candidate ligand is a GPCR ligand. In one such example, the administration of a GPCR ligand may cause an increase in expression of the reporter gene ranging from at least about a 2-fold increase in expression to at least about a 100-fold increase in expression, when compared to the reporter gene expression of the cell before the administration of the GPCR ligand. In particular examples, a positive GPCR ligand may cause an increase in reporter gene expression of approximately 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 35-fold, 40-fold, 45-fold, 50-fold, 55-fold, 60-fold, 65-fold, 70-fold, 75-fold, 80-fold, 95-fold, and 100-fold. The detection of reporter gene expression as described in the methods provided herein, may include direct or indirect detection of the reported gene using suitable methods known in the art. For example, the expression of the reporter gene may be detected by an enzymatic activity assay, histochemical staining, fluorescence, or an enzyme immunoassay such as an enzyme-linked immunosorbent assay (ELISA).

Where the methods described herein involve a cell-based assay for screening and identifying GPCR ligands, the cells utilized in the assay may be cells selected from those cell lines that are appropriate for a high throughput cAMP-dependent assay. In one such embodiment of the methods disclosed herein, the cell-based assay may use human embryonic kidney 293 cells (HEK-293). Other suitable assays could involve other cells that can be transfected including primary cells (cells derived from mammals, yeast and other eukaryotes as well as prokaryotes. Other cell lines could be used, including but not limited to Cos 7, 3T3, Jurkat, CHO, HeLa, and cultured cells described by the National Cancer Institute's 60 cancer lines, Mutants or derivatives of various cell lines could be used. In particular embodiments of the methods, the cell-based assay for screening and identifying GPCR ligands may use a cell line that transiently expresses a desired GPCR and/or a chimeric G protein. In other particular embodiments of the methods, the cell-based assay for screening and identifying GPCR ligands may use a cell line that stably expresses a desired GPCR and/or a chimeric G protein. In further embodiments, the cells utilized in the methods described herein include cells that express GPCR and chimeric G proteins over a suitable period of time and in amounts that allow the execution of the methods described herein.

In certain embodiments, the methods disclosed herein include a cell-based assay utilizing cells that express GPCRs that do not normally couple to $G\alpha_s$ subunits. In particular embodiments, the methods disclosed herein comprise the use of GPCRs selected from M2AchR, 5-HT1B, dopamine D4, β2-adrenergic, GNRH, neuropeptide Y1, leukotriene B4, P2Y6, Rho20-eugenol, T1R2, and T1R3. In other particular embodiments, the GPCRs for use in the methods disclosed herein may include These chimeras have also been used for FPRs (formyl peptide receptors) and three subtypes of opioid receptors (delta, kappa, mu).

The methods disclosed herein include methods for screening and identifying ligands of GPCRs that are GPCR antagonists. In certain embodiments, the methods disclosed herein include methods for the identification of antagonists of GPCRs that inhibit the activation of GPCRs and their coupled G proteins. In other embodiments, such methods include an assay for screening and identifying GPCR ligands that are GPCR antagonists by using a cAMP detection system, wherein GPCR ligand binding inhibits the activation of a $G\alpha_s$-based chimeric G protein that, in turn, does not stimulate adenylyl cyclase and thus, does not increase cAMP. In yet other embodiments, the methods disclosed herein may be used to identify ligands that decrease signaling of GPCRs expressed and present in cells at normal (basal) levels or in cells in which the levels of the target GPCR have been elevated through over-expression of the target receptor.

The methods disclosed herein may also be used for the characterization of orphan GPCRs. In certain such embodiments, the methods disclosed herein comprise a cell-based assay with a cell line cotransfected with (i) an orphan GPCR of interest, (ii) a Gαs-based chimeric G protein as described herein, and (iii) a cAMP detection system, as described herein, wherein GPCR ligand binding leads to identification of a ligand for the orphan GPCR. Examples of orphan GPCRs that may be used with the methods disclosed herein may include Gpr88, Gpr101, Gpr149, Gpr56, Gpr6, Gpr83, Gpr50, Gpr139, Gpr151, Gpr165, Gpr171, Gpr177, Gpr153, Gpr176, and Gpr161, based on their pattern of expression in the brain. As additional knowledge is gained about potential functions of these and other individual orphan GPCRs, the G-protein chimeras disclosed herein may be useful to screen for molecules that activate or inhibit these GPCRs. The G-protein chimeras disclosed herein are also useful in developing assays to screen for molecules such as agonists, partial agonists, antagonists, and inverse agonists of GPCRs.

III. $G\alpha_s$-BASED CHIMERIC G PROTEINS

The present disclosure includes $G\alpha_s$-based chimeric G proteins that may promiscuously bind to a variety of GPCRs. In one embodiment, the $G\alpha_s$-based chimeric G proteins comprise the substitution of the C-terminal amino acids of a $G\alpha_s$ subunit, such as, for example, a rat $G\alpha_s$ subunit (SEQ ID NO: 1), with the C-terminal amino acids of a different Gα subunit. The substitution of the C-terminal amino acids of $G\alpha_s$ with the C-terminal amino acids of a different Gα subunit allow the $G\alpha_s$-based chimera to promiscuously couple with a variety GPCRs that would not normally couple with $G\alpha_s$. In such embodiments, at least 1, 2, 3, 4, 5, 6, 7, 8, 9, 10, 11, 12, 13, 14, 15, 16, 17, 18, 19, 20, or more, C-terminal amino acids of a $G\alpha_s$ subunit may be substituted with the desired C-terminal acids of a different Gα subunit. In certain such embodiments, the C-terminal amino acid substitutions include an amino acid substitution of about 2-5, 2-10, 2-13, 2-15, 5-10, 5-15, 5-20, 10-15, and 10-20 of the C-terminal amino acids of the $G\alpha_s$ subunit.

In particular embodiments of the chimeric G proteins disclosed herein, the one or more of the C-terminal amino acids of a $G\alpha_s$ subunit, such as, for example, a rat $G\alpha_s$ subunit (SEQ ID NO: 1), may be substituted with one or more of the C-terminal amino acids from a $G\alpha_o$ subunit, $G\alpha_z$ subunit, $G\alpha_t$ subunit, $G\alpha_q$ subunit, $G\alpha_{15}$ subunit, $G\alpha_i$ subunit, or $G\alpha_k$ subunit. For example, the C-terminal amino acids of a $G\alpha_s$ subunit may be substituted with at least 1, 2, 3, 4, 5, 6, 7, 8, 9, 10, 11, 12, 13, 14, 15, 16, 17, 18, 19, and 20 amino acids selected from a $G\alpha_o$ subunit, $G\alpha_z$ subunit, $G\alpha_t$ subunit, $G\alpha_q$ subunit, $G\alpha_{15}$ subunit, $G\alpha_i$ subunit, or $G\alpha_k$ subunit. Alternatively, the C-terminal amino acids of a $G\alpha_s$ subunit may be substituted with at least about 2-5, 2-10, 2-13, 2-15, 5-10, 5-15, 5-20, 10-15, and 10-20 of the C-terminal amino acids selected from a $G\alpha_o$ subunit, $G\alpha_z$ subunit, $G\alpha_t$ subunit, $G\alpha_q$ subunit, $G\alpha_{15}$ subunit, $G\alpha_i$ subunit, or $G\alpha_k$ subunit. In particular embodiments, the chimeric G proteins described herein may include a $G\alpha_s$-based chimeric G protein selected from $G\alpha_s$-$G\alpha_k$-5 (SEQ ID NO: 2), $G\alpha_s$-$G\alpha_t$-13 (SEQ ID NO: 3), $G\alpha_s$-$G\alpha_o$-13 (SEQ ID NO: 4), $G\alpha_s$-$G\alpha_i$-13 (SEQ ID NO: 5), $G\alpha_s$-$G\alpha_z$-13 (SEQ ID NO: 6), $G\alpha_s$-$G\alpha_{15}$-13 (SEQ ID NO: 7), and $G\alpha_s$-$G\alpha_q$-13 (SEQ ID NO: 8).

As this specification discusses various chimeric G proteins and chimeric G protein sequences, it is understood that genes, nucleotide sequences, cDNA, and DNA constructs that may code for, or that may be used to express, the $G\alpha_s$-based chimeric G proteins are disclosed herein. This would include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

Nucleotide sequences encoding the $G\alpha_s$-based chimeras may be prepared according to recombinant DNA techniques and methods well known in the art, or through direct synthesis of chimeric G-protein sequences. In one example, the nucleotides encoding the $G\alpha_s$-based chimeras may be prepared by substituting the 3' nucleotides of a $G\alpha_s$ subunit with the 3' nucleotides from a different Gα subunit that encode the selected C-terminal amino acids of the chimeric protein. In particular examples, the nucleotides encoding the $G\alpha_s$-based chimeras may be prepared using the nucleotide sequences useful for expressing Gα subunits selected from $G\alpha_s$, $G\alpha_i$, $G\alpha_t$, $G\alpha_o$, $G\alpha_z$, $G\alpha_{15}$, $G\alpha_k$, and $G\alpha_q$ subunits.

In one embodiment, the nucleotide sequences disclosed herein may be inserted into an expression vector for expression of the $G_{\alpha s}$-based chimeric G proteins. In one such embodiment, the expression vector may be a plasmid comprising an insert of cDNA that encodes the $G_{\alpha s}$-based chimeric G proteins disclosed herein. In one such particular embodiment, the expression vector is a pcDNA3.1(−) (Invitrogen) plasmid expression vector. For example, the $G_{\alpha s}$- based chimera expression vector may be prepared by inserting cDNA encoding the desired $G_{\alpha s}$-based chimera into a plasmid such as pcDNA3.1(–). In another embodiment, the nucleotide sequences disclosed herein may be part of an expression vector or DNA construct transfected into a cell for the expression of the $G_{\alpha s}$-based chimeric G proteins.

The practice of the present invention employs, unless otherwise indicated, conventional techniques of chemistry, molecular biology, microbiology, recombinant DNA, genetics, immunology, cell biology, cell culture and transgenic biology, which are within the skill of the art. (See, e.g., Maniatis, T., et al. (1982) Molecular Cloning: A Laboratory Manual (Cold Spring Harbor Laboratory, Cold Spring Harbor, N.Y.); Sambrook, J., et al. (1989) Molecular Cloning: A Laboratory Manual, $2^{nd}$ Ed. (Cold Spring Harbor Laboratory, Cold Spring Harbor, N.Y.); Ausubel, F. M., et al. (1992) Current Protocols in Molecular Biology, (J. Wiley and Sons, NY); Glover, D. (1985) DNA Cloning, I and II (Oxford Press); Anand, R. (1992) Techniques for the Analysis of Complex Genomes, (Academic Press); Guthrie, G. and Fink, G. R. (1991) Guide to Yeast Genetics and Molecular Biology (Academic Press); Harlow and Lane (1988) Antibodies: A Laboratory Manual (Cold Spring Harbor Laboratory, Cold Spring Harbor, N.Y.); Jakoby, W. B. and Pastan, I. H. (eds.) (1979) Cell Culture. Methods in Enzymology, Vol. 58 (Academic Press, Inc., Harcourt Brace Jovanovich (NY); Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Hogan et al. (eds) (1994) Manipulating the Mouse Embryo; A Laboratory Manual, $2^{nd}$ Edition, Cold Spring Harbor Laboratory Press, Cold Spring Harbor, N.Y.).

The following examples are provided merely as illustrative of various aspects of the invention and shall not be construed to limit the invention. It is to be understood that the disclosed compositions and methods are not limited to the particular methodologies, protocols, and reagents described herein. In each instance, unless otherwise specified, standard materials and methods were used in carrying out the work described in the Examples provided. All patent and literature references cited in the present specification are hereby incorporated herein by reference in their entirety.

EXAMPLES

Example 1—A High Throughput Reporter Gene Assay for Detecting the Activation of $G\alpha_s$-Coupled GPCRs A high throughput screening assay was investigated for $G\alpha_s$-coupled GPCRs based on the CRE-SEAP reporter gene construct, in which five tandem cAMP response elements (GREs) lie upstream of a gene encoding secreted alkaline phosphatase (SEAP) (Durocher et al., Anal Biochem 284: 316-326 (2000)). To ensure the general utility of the CRE-SEAP reporter gene construct for the detection of $G\alpha_s$-coupled GPCR activation, HEK-293 cells were cotransfected with the CRE-SEAP construct together with expression vectors encoding either a β2-adrenergic receptor or an odorant receptor (OR) that recognizes vanillin and eugenol. Both receptors are GPCRs that couple to $G\alpha_s$ subunits. The HEK-293 cells expressing the β2-adrenergic receptor were grown for 48 hours in the presence or absence of 10 uM isoproterenol. The HEK-293 cells expressing the OR were grown for 48 hours in the presence of 500 uM eugenol. After growing in the presence of the ligands, the cells were assayed for SEAP activity using a fluorescent alkaline phosphatase substrate and a fluorescence plate reader. As shown in FIG. 1(a), both the β2-adrenergic receptor expressing cells and the OR expressing cells, showed an increase in SEAP activity. Therefore, the CRE-SEAP reporter gene is generally usable for the detection of $G\alpha_s$-coupled GPCR activation.

Materials and Methods

GPCR cloning: Human β2-adrenergic receptor was cloned by PCR from cDNA templates (ATCC) and ligated into pcDNA 3.1(–) for expression in HEK-293 cells. The Rho20-eugenol receptor contained the first twenty amino acids of rhodopsin and a three amino acid linker 5' to the full-length odorant receptor (OR), which was cloned from genomic DNA.

CRE-SEAP Reporter Gene Assay: $0.5 \times 10^5$ HEK-293 cells (ATCC) were seeded into each well of a 96 well plate 24 hours prior to transfection. cDNAs encoding GPCRs and SEAP reporters (Mercury Pathway Profiling System, BD Biosciences) were transfected into HEK-293 cells using lipofectamine reagent (Invitrogen) according to the manufacturer's protocols. 20 ng GPCR cDNA and 20 ng CRE-SEAP cDNA were transfected into each well of the 96 well plate.

Following transfection, the cells were maintained for 48 hours in 200 ul serum free media containing either 10 uM isoproterenol (Sigma) or 500 uM eugenol (Sigma). The plates were wrapped in plastic film and heated to 65-70° C. for 2 hours to kill endogenous phosphatases. The plates were then cooled to room temperature, and 100 ul of the supernatant was transferred to a new 96 well plate. 100 ul of substrate solution was added to each well. The substrate solution was 1.2 mM 4-methylumbelliferyl phosphate (Sigma) in 2 M diethanolamine bicarbonate, pH 10.0 (dry ice used to adjust pH). Fluorescence was then measured using a CytoFluor 4000 multi well plate reader (Applied Biosystems).

Example 2—$G\alpha_s$-Based Chimeric G Proteins with Promiscuous GPCR Coupling $G\alpha_s$-based chimeric G proteins that promiscuously bind to a variety of GPCRs were used to provide a high throughput CRE-SEAP reporter gene assay useful for identifying ligands of GPCRs that do not normally couple to $G\alpha_s$.

The constructs encoding chimeric G proteins were made by substituting C-terminal amino acids of $G\alpha_s$ (SEQ ID NO: 1) with the corresponding C-terminal amino acid sequences of other Gα subunits. A first set of $G\alpha_s$-based chimeric G proteins was prepared by designing constructs encoding seven $G\alpha_s$-$G\alpha_i$ chimeras in which the C-terminal 5, 11, 13, 28, 65, 84, or 131 amino acids of $G\alpha_s$ were substituted with the corresponding C-terminal amino acids from the $G\alpha_o$ subunit. Briefly, HEK-293 cells were cotransfected with chimera constructs together with the CRE-SEAP reporter gene construct and a cDNA encoding the M2 muscarinic acetylcholine receptor (M2AchR), a GPCR that couples to Gα$_o$ but not to Gα$_s$ and inhibits cAMP production. The transfected cells were cultured in the presence or absence of acetylcholine and then assayed for SEAP activity.

Figure 1B:
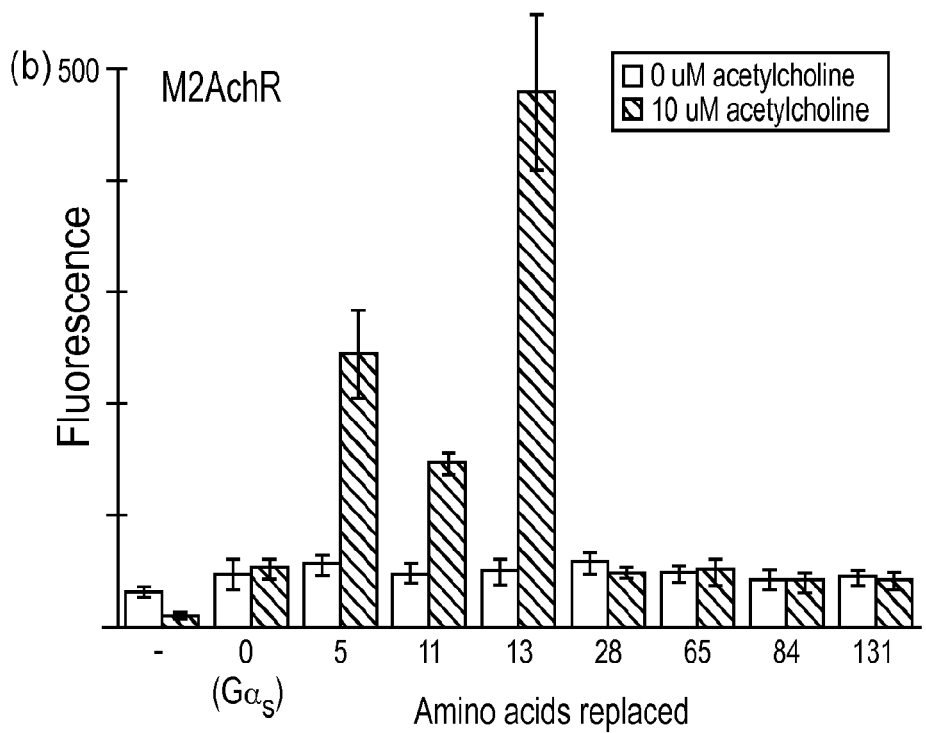

As shown in FIG. 1(b), the Gα$_s$-Gα$_i$ chimeric G protein constructs allowed ligand induced increases in SEAP activity mediated by M2AchR. Particularly effective were the Gα$_s$-Gα$_i$-5, Gα$_s$-Gα$_i$-11, and Gα$_s$-Gα$_i$-13 (SEQ ID NO: 5) constructs. Cells cotransfected with Gα$_s$-Gα$_i$-13, M2AchR, and CRE-SEAP displayed a 10-fold increase in SEAP activity in response to 10 uM acetylcholine. Control cells transfected with only CRE-SEAP and G protein constructs gave no response to acetylcholine. The results showed that Gα$_s$-Gα$_i$ G protein chimeras promiscuously couple to a non-Gα$_s$ GPCR, switching M2AchR from a receptor that normally inhibits cAMP production to a receptor that stimulates cAMP production. The results also show the effectiveness of the CRE-SEAP reporter gene construct as a high throughput assay for detecting the activation GPCRs that couple with Gα$_s$-based G protein chimeras.

Figure 1C:
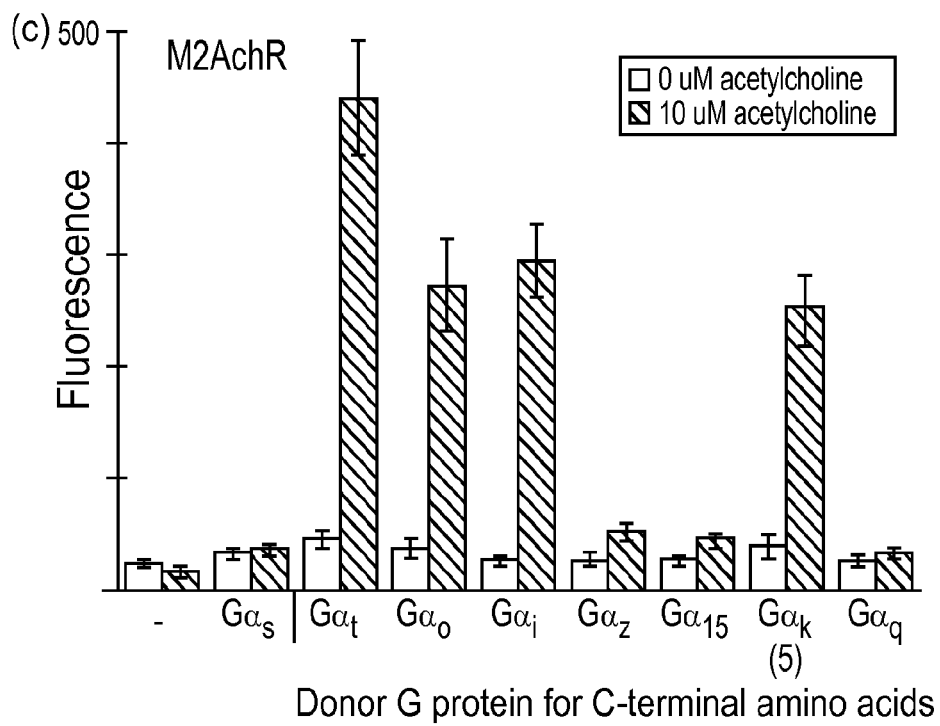

A series of chimeric constructs were prepared in which the final 13 C-terminal amino acids of the Gα$_s$ subunit were substituted with the final 13 C-terminal amino acids from Gα$_o$, Gα$_z$, Gα$_t$, Gα$_q$, or Gα$_{15}$ subunits. Also tested were the Gα$_s$-Gα$_i$-13 and a chimera containing the last 5 C-terminal amino acids of Gα$_k$ (Gα$_s$-Gα$_k$-5 (SEQ ID NO: 2)). These chimeric constructs were tested for coupling with M2AchR. As shown in FIG. 1(c), Gα$_s$-Gα$_t$-13 (SEQ ID NO: 3), Gα$_s$-Gα$_o$-13 (SEQ ID NO: 4), Gα$_s$-Gα$_i$-13 (SEQ ID NO: 5), and Gα$_s$-Gα$_k$-5 (SEQ ID NO: 2) permitted approximately a 6-fold to 10-fold increase in SEAP activity in response to the 10 uM acetylcholine ligand, Gα$_s$-Gα$_i$-13 and Gα$_s$-Gα$_t$-13 showing the highest responses. The Gα$_s$-Gα$_o$-13 (SEQ ID NO: 6) and Gα$_s$-Gα$_{15}$-13 (SEQ ID NO: 7) allowed approximately 2-fold increases in SEAP activity. These results show that multiple Gα$_s$-based chimeric G proteins promiscuously couple with M2AchR. The results also show that the Gα$_s$-based chimeric G proteins retain the ability to stimulate adenylyl cyclase as evidenced by the increase in SEAP.

Material and Methods

Chimeric G protein cloning: An insert containing rat Gα$_s$ cDNA was cut out using the restriction enzymes SalI and HinDIII, and ligated into pcDNA3.1(-) cut with XhoI and HinDIII. The chimeric G proteins with the desired C-terminal amino acid substitutions were prepared by PCR using Gα$_s$ as a template. More specifically, Gα$_s$ was PCR amplified between an internal EcoRI site and the stop codon, with a 3' HinDIII placed immediately after the stop codon. A different 3' oligonucleotide was used for each Gα$_s$ chimera and contained a 39 bp sequence that encoded the substituted amino acids at the C-terminus selected from the donor Gα subunit.

M2AchR GPCR cloning: Rat M2AchR receptor was cloned by PCR from cDNA templates (ATCC) and ligated into pcDNA 3.1(-) for expression in mammalian cells.

CRE-SEAP Reporter Gene Assay: 0.5×10$^5$ HEK-293 cells (ATCC) were seeded into each well of a 96 well plate 24 hours prior to transfection. cDNAs encoding M2AchR, SEAP reporters (Mercury Pathway Profiling System, BD Biosciences), and G protein chimeras were transfected into HEK-293 cells using lipofectamine reagent (Invitrogen) according to the manufacturer's protocols. 20 ng M2AchR cDNA, 20 ng CRE-SEAP cDNA, and 0.5 ng G protein chimera cDNA were transfected into each well of the 96-well plate.

Following transfection, the cells were maintained for 48 hours in 200 ul serum free media containing 10 uM acetylcholine (Sigma). The plates were wrapped in plastic film and heated to 65-70° C. for 2 hours to kill endogenous phosphatases. The plates were then cooled to room temperature, and 100 ul of the supernatant was transferred to a new 96 well plate. 100 ul of substrate solution was added to each well. The substrate solution was 1.2 mM 4-methylumbelliferyl phosphate (Sigma) in 2 M diethanolamine bicarbonate, pH 10.0 (dry ice used to adjust pH). Fluorescence was then measured using a CytoFluor 4000 multi well plate reader (Applied Biosystems).

Example 3—Coupling of Gα$_s$-Based Chimeric G Proteins with a Variety of GPCRs

The coupling of Gα$_s$-based chimeric G proteins with GPCRs that do not bind to Gα$_s$ was explored. The GPCRs examined were those that couple with Gα$_i$/Gα$_o$ subunits (serotonin 1b, neuropeptide Y1, leukotriene B4, and dopamine D4), Gα$_q$ (GNRH, UDP, and calcium-sensing receptors), and the orphan mammalian sweet taste receptor complex (T1R2 and T1R3) with unknown coupling preference. The Gα$_s$-based chimeric G proteins examined in this example were Gα$_s$-Gα$_i$-5, Gα$_s$-Gα$_t$-13 (SEQ ID NO: 3), Gα$_s$-Gα$_o$-13 (SEQ ID NO: 4), Gα$_s$-Gα$_i$-13 (SEQ ID NO: 5), Gα$_s$-Gα$_z$-6 (SEQ ID NO: 18), Gα$_s$-Gα$_{15}$-13 (SEQ ID NO: 7), Gα$_s$-Gα$_k$-5 (SEQ ID NO: 2), and Gα$_s$-Gα$_q$-13 (SEQ ID NO: 8). The chimeric G protein constructs were prepared as described herein. For the coupling assay, HEK-293 cells were cotransfected with each of the Gα$_s$-based chimeric G protein constructs of interest together with the CRE-SEAP reporter gene construct and a cDNA encoding the GPCR to be tested. The transfected cells were cultured in the presence or absence of a GPCR ligand and then assayed for SEAP activity.

As shown in FIG. 2, each of the GPCRs examined coupled productively with at least one of the Gα$_s$-based chimeric G proteins. No ligand-induced increases in SEAP activity were seen in cells transfected with only CRE-SEAP and chimeric G protein constructs, indicating that any observed effects were dependent on the transfected receptor (data not shown). All but one (dopamine D4) of the GPCRs tested coupled to the Gα$_s$-Gα$_t$-13 chimeric protein. The Gα$_s$-Gα$_i$-13 and Gα$_s$-Gα$_o$-13 chimeras each coupled to seven of the nine GPCRs. Gα$_s$-Gα$_o$-13 permitted a response with the dopamine D4 receptor, one GPCR that did not couple with Gα$_s$-Gα$_t$-13. These studies indicate that the Gα$_s$-Gα$_t$-13 chimera is particularly promiscuous and couples to a large variety of GPCRs. However, the other chimeras are also useful and may permit assays of GPCRs that interact poorly or not at all with Gα$_s$-Gα$_t$-13.

Figure 2A:
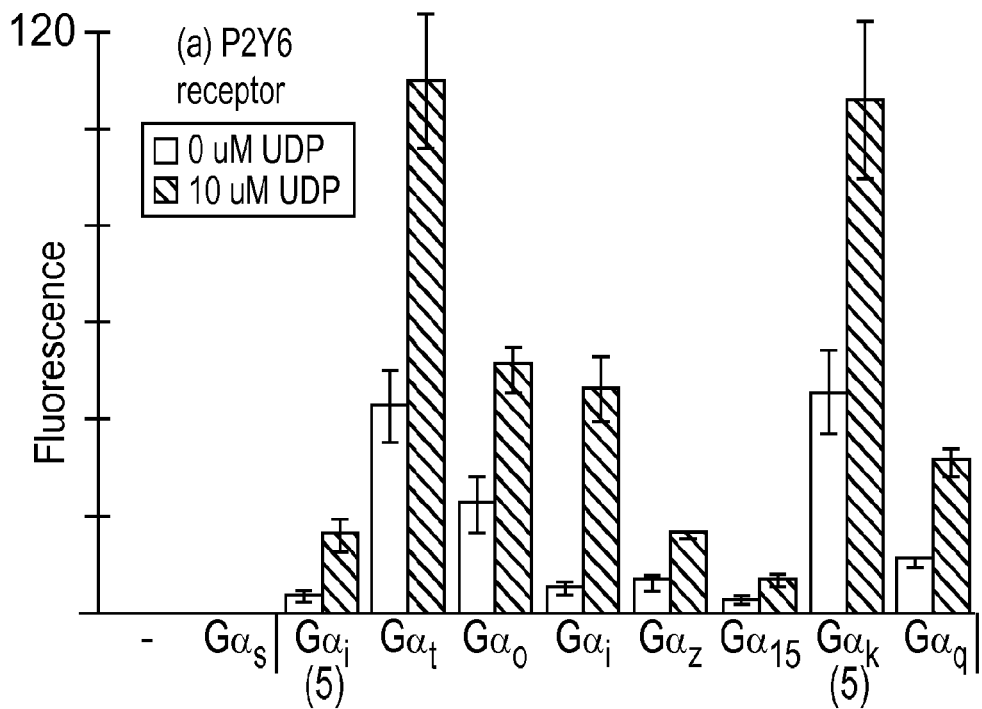
FIG. 2 shows the results of testing for the coupling of various GPCRs with unsubstituted $G\alpha_s$ compared to $G\alpha_s$-based chimeric proteins according to the present description with C-terminal amino acids substituted with the C-terminal amino acids of other Gα subunits.
Figure 2B:
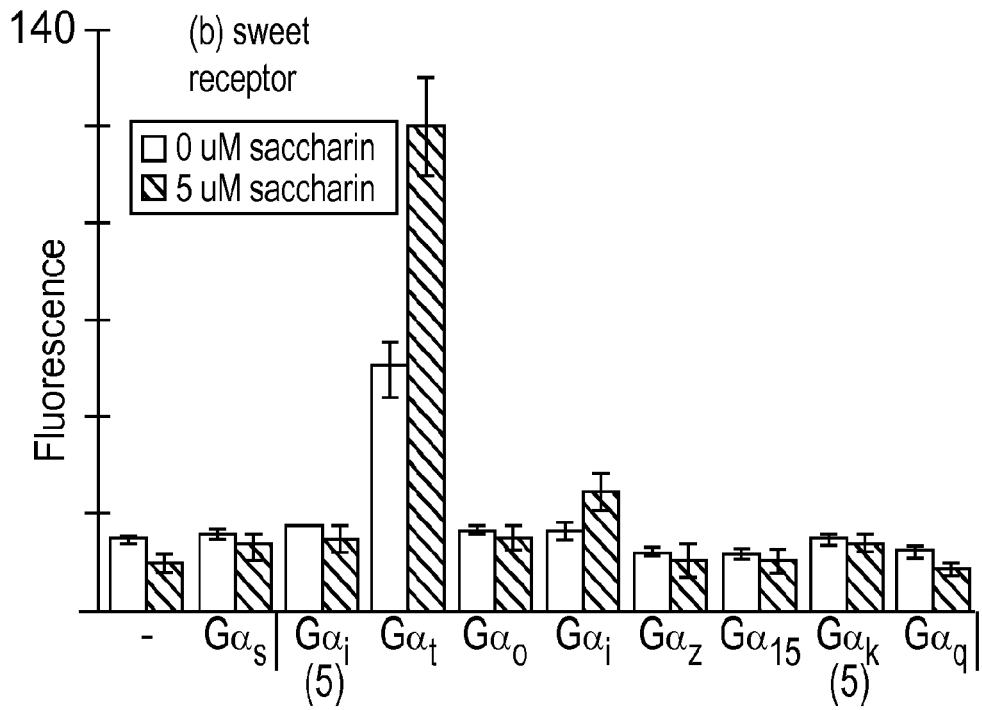
Figure 2C:
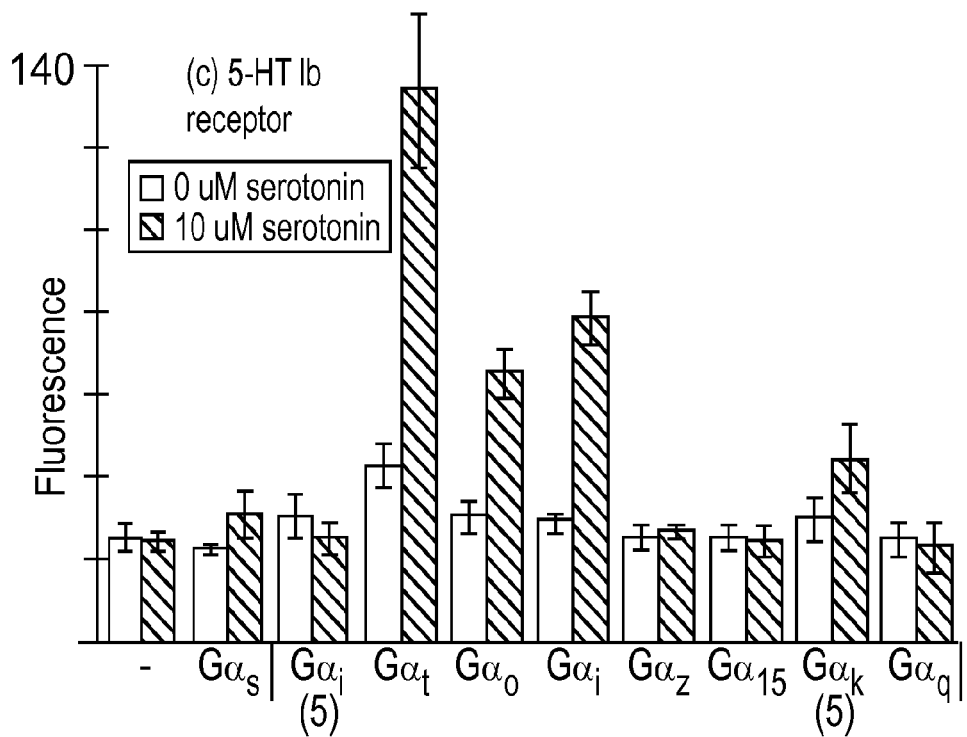
Figure 2D:
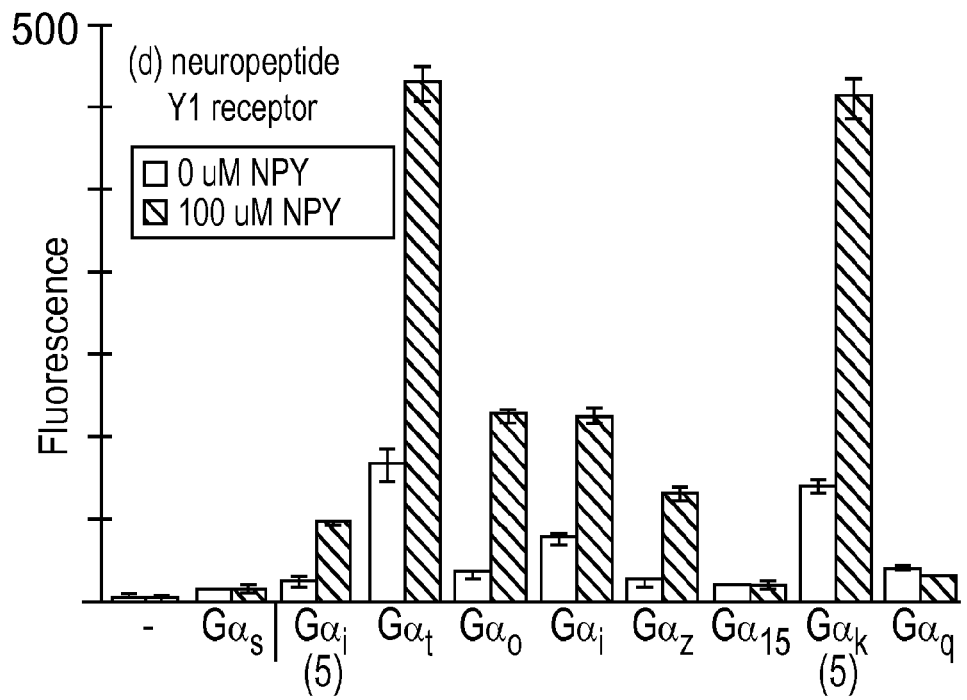
Figure 2E:
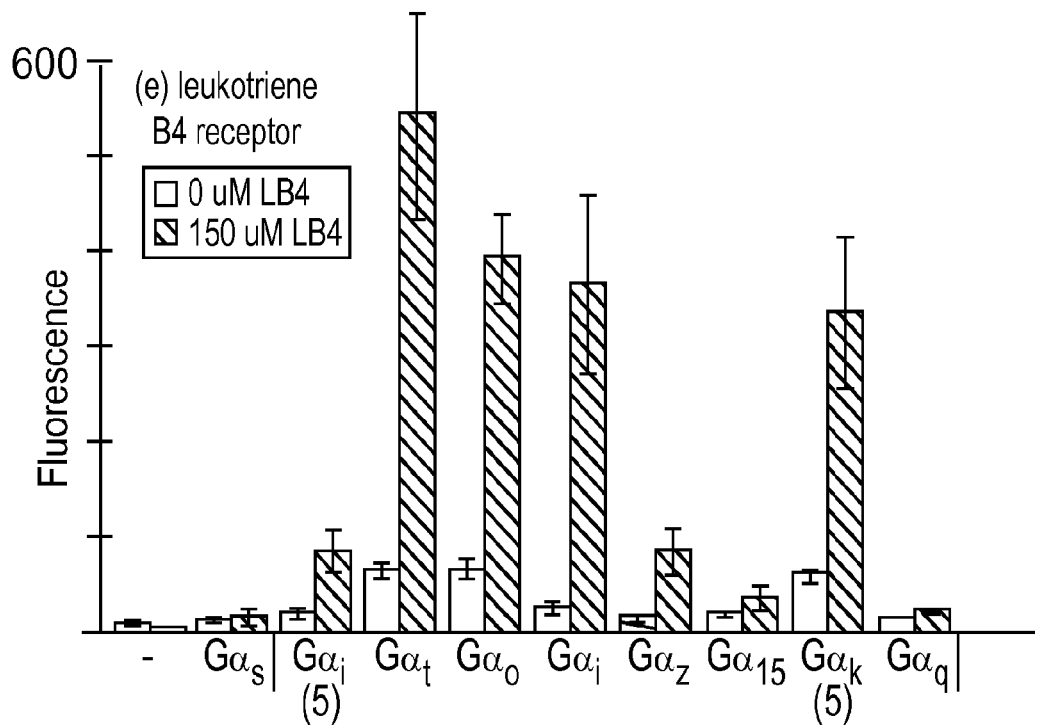
Figure 2F:
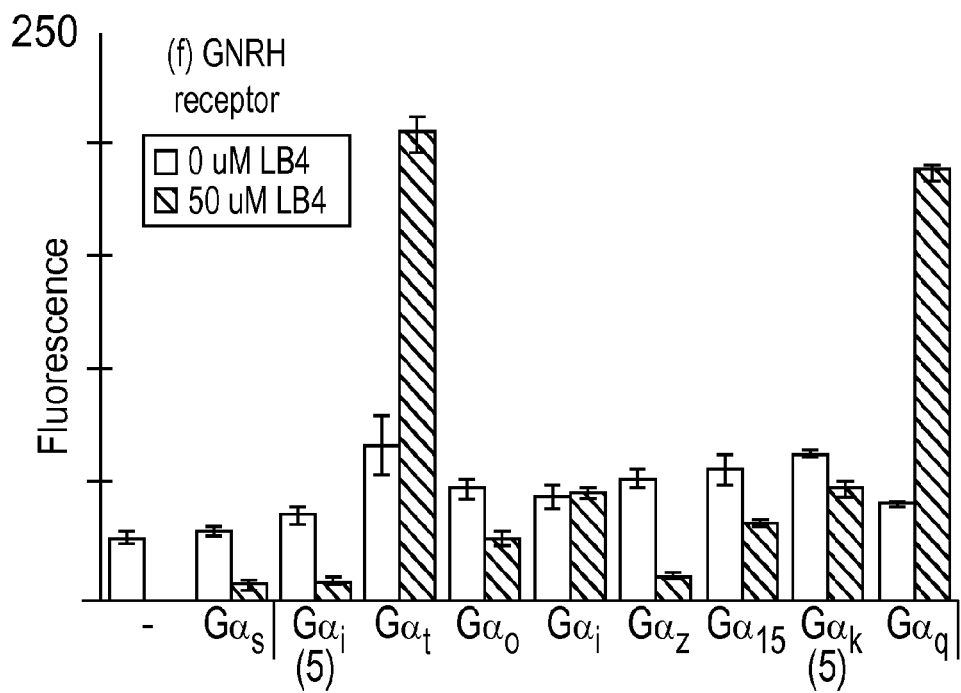
Figure 2G:
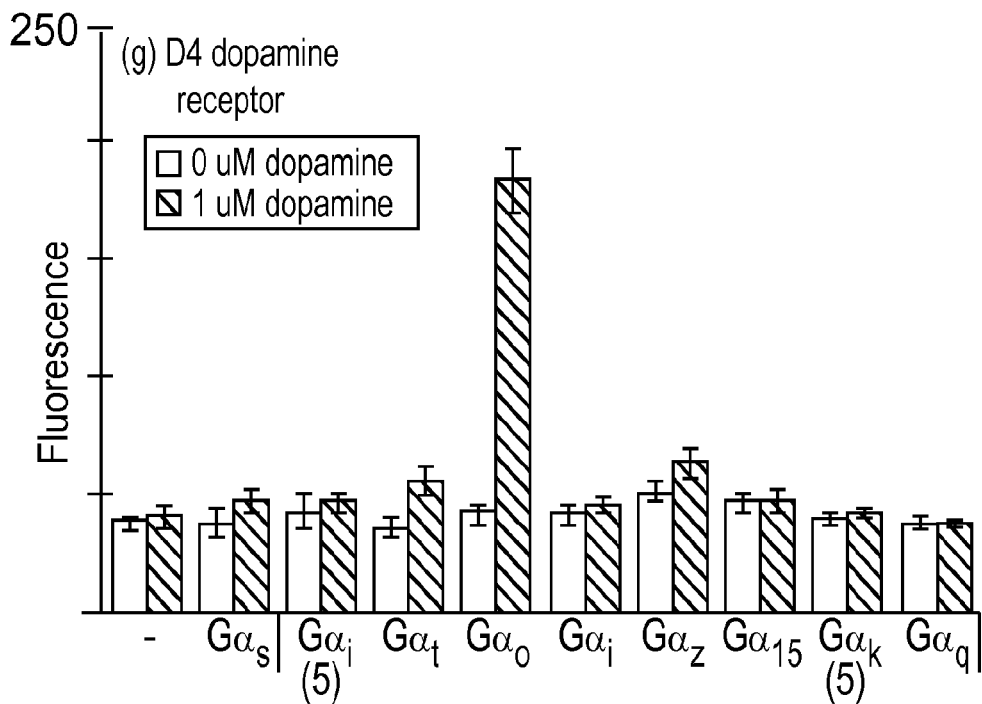
Figure 2H:
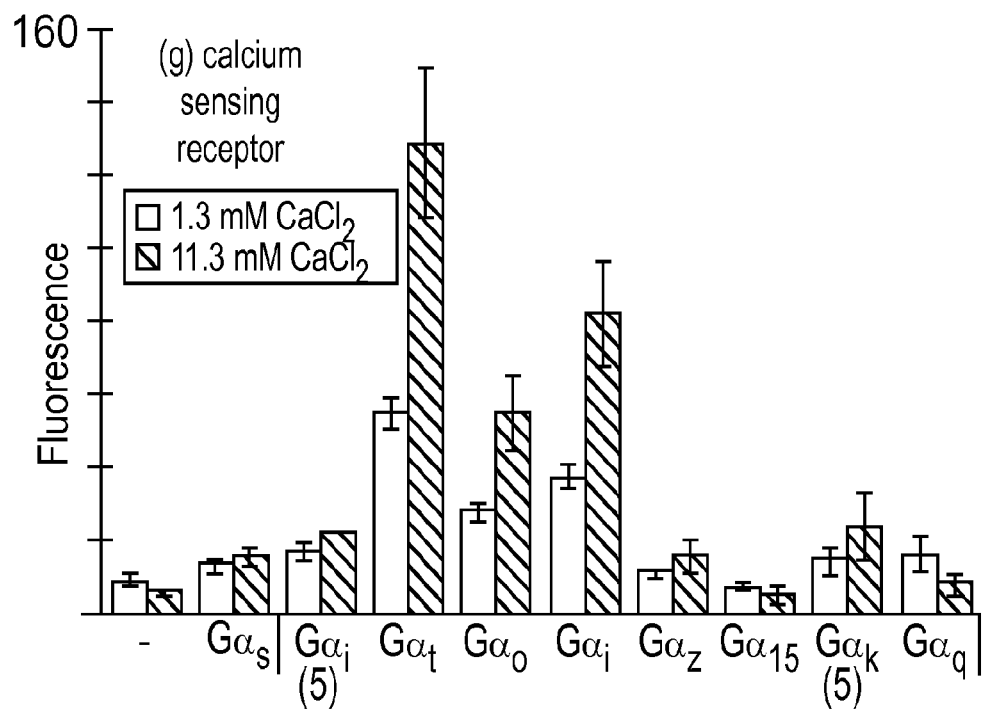

Also tested was whether the chimeric G proteins disclosed herein can be used to detect the activation of GPCRs whose G protein coupling preference is unknown, as is the case with orphan GPCRs. One receptor of unknown G protein coupling preference is the sweet receptor heterodimer (T1R2/T1R3). We found that the sweet receptor, which is activated by 5 mM saccharin, can couple to Gα$_s$-Gα$_t$-13 (FIG. 2b). The resulting increase in SEAP activity (about two fold) is dependent on cotransfection of constructs encoding both T1R2 and T1R3, consistent with the requirement for receptor heterodimerization. These results demonstrate the utility of Gα$_s$-based chimeric G proteins, such as Gα$_s$-Gα$_t$-13, as promiscuous G proteins for high throughput screening of GPCR ligands.

Materials and Methods

Chimeric G protein cloning: An insert containing rat Gα$_s$ cDNA was cut out using the restriction enzymes SalI and HinDIII, and ligated into pcDNA3.1(-) cut with XhoI and HinDIII. The chimeric G proteins with the desired C-terminal amino acid substitutions from the $G\alpha_i$, $G\alpha_t$, $G\alpha_o$, $G\alpha_z$, $G\alpha_{15}$, $G\alpha_k$, and $G\alpha_q$ were prepared by PCR using $G\alpha_s$ as a template. More specifically, $G\alpha_s$ was PCR amplified between an internal EcoRI site and the stop codon, with a 3' HinDIII placed immediately after the stop codon. A different 3' oligonucleotide was used for each $G\alpha_s$ chimera and contained a 39 bp sequence that encoded the substituted amino acids at the C-terminus selected from the donor $G\alpha$ subunit.

GPCR cloning: Mouse 5-HT1B, mouse dopamine D4, human GNRH, and human neuropeptide Y1 receptors were cloned by PCR from cDNA templates (ATCC) and ligated into pcDNA 3.1(−) (Invitrogen) for expression in mammalian cells. Mouse Leukotriene B4 and P2Y6 receptors were cloned by PCR from genomic DNA and ligated into pcDNA 3.1(−) as well. T1R2 and T1R3 expression constructs were previously described (Montmayeur et al., Nat Neurosci 4: 492-498 (2001)).

CRE-SEAP Reporter Gene Assay: $0.5 \times 10^5$ HEK-293 cells (ATCC) were seeded into each well of a 96 well plate 24 hours prior to transfection. cDNAs encoding GPCRs, SEAP reporters (Mercury Pathway Profiling System, BD Biosciences), and G protein chimeras were transfected into HEK-293 cells using lipofectamine reagent (Invitrogen) according to the manufacturer's protocols. 20 ng GPCR cDNA and 20 ng CRE-SEAP cDNA, and 0.5 ng G protein chimera cDNA were transfected into each well of the 96-well plate. For the sweet receptor experiments, 5 ng T1R2, 20 ng T1R3, 20 ng CRE-SEAP, and 0.5 ng $G\alpha_s$-$G\alpha_t$ cDNA were used.

Following transfection, the cells were maintained for 48 hours in 200 ul serum free media containing GPCR ligand. The, ligand concentrations used were 10 uM serotonin (Sigma), 5 mM saccharin (Sigma), 10 mM acesulfame K (Fluka), 10 uM UDP (P2Y6 ligand) (Sigma), 150 nM leukotriene B4 (Calbiochem), 50 nM GNRH (Sigma), 1 uM dopamine (Sigma), 100 nM neuropeptide Y (Sigma) and 10 mM calcium chloride (Sigma). The plates were wrapped in plastic film and heated to 65-70° C. for 2 hours to kill endogenous phosphatases. The plates were then cooled to room temperature, and 100 ul of the supernatant was transferred to a new 96 well plate. 100 ul of substrate solution was added to each well. The substrate solution was 1.2 mM 4-methylumbelliferyl phosphate (Sigma) in 2 M diethanolamine bicarbonate, pH 10.0 (dry ice used to adjust pH). Fluorescence was then measured using a CytoFluor 4000 multi well plate reader (Applied Biosystems).

Example 4—Stably Expressed $G\alpha_s$-Based Chimeric G Proteins

Figure 3:
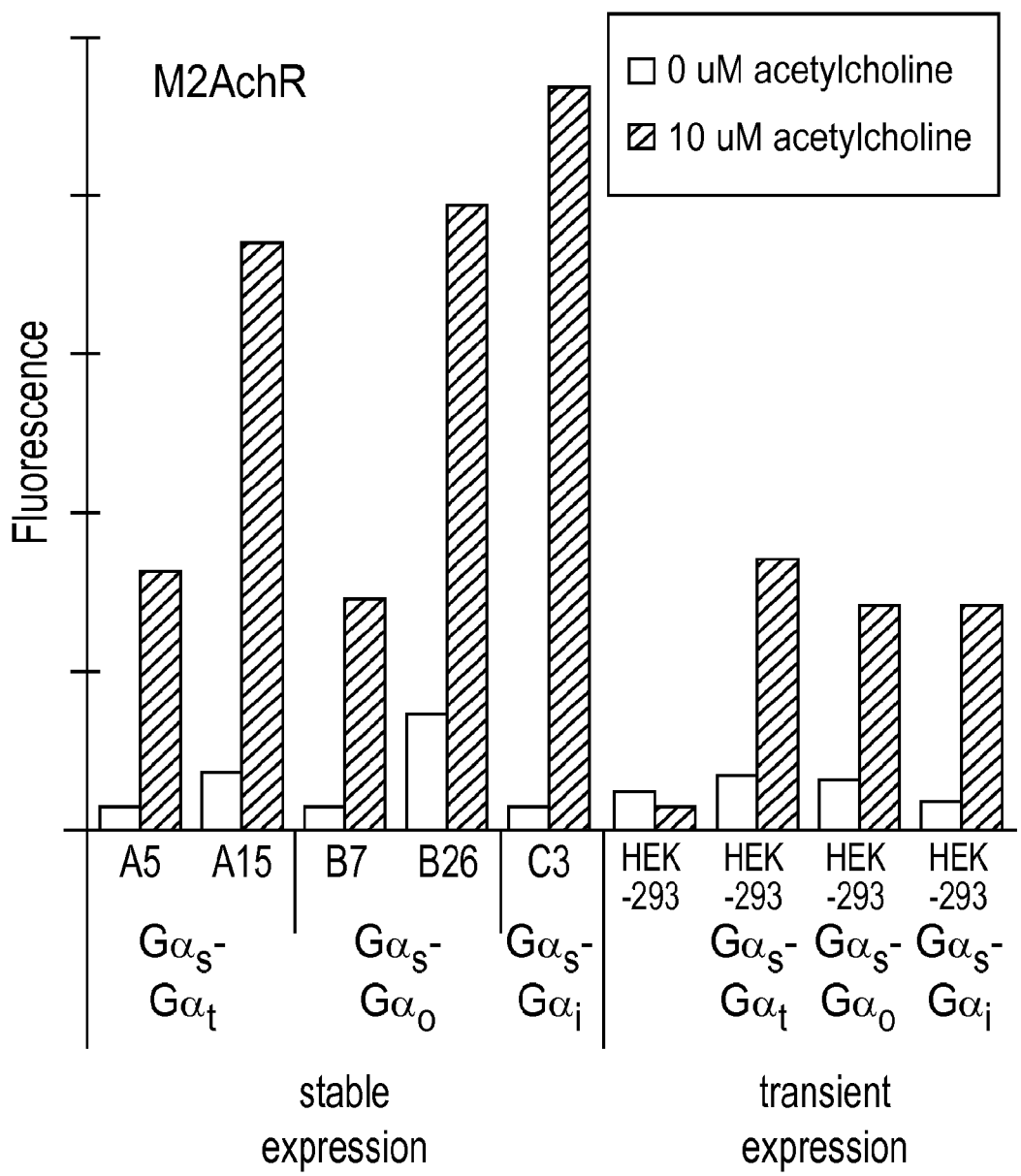
FIG. 3 shows the results of testing for the coupling of the M2AchR GPCR in cells with stably expressed chimeric G proteins according to the present description compared with the results in cells with transiently expressed chimeric G proteins.

The ligand-induced SEAP activity for cells stably transfected and expressing $G\alpha_s$-based chimeric G proteins was compared with that of cells transiently expressing $G\alpha_s$-based chimeric G proteins. Stable expression is achieved by integration of the construct of interest into the target cell's chromosome. Cell lines were prepared that stably expressed $G\alpha_s$-$G\alpha_t$-13, $G\alpha_s$-$G\alpha_i$-13, and $G\alpha_s$-$G\alpha_o$-13 G protein chimeras. As shown in FIG. 3, levels of SEAP activity were greater in cell stably expressing the G protein chimeras than cells transiently expressing G protein chimeras. For the $G\alpha_s$-$G\alpha_t$-13 chimera, activation of M2AchR in cells stably expressing the chimera showed an approximately 30-fold to 80-fold increase in SEAP activity. Cells transiently expressing the $G\alpha_s$-$G\alpha_t$-13 chimera construct showed an approximately 10-fold increase in SEAP activity. Therefore, cell lines stably expressing the $G\alpha_s$-based chimeric G proteins can provide enhanced sensitivity for the screening and identification of GPCR ligands.

Materials and Methods

Preparation of cells stably expressing G protein chimeras: HEK-293 cells were transfected with each of the G protein chimeras of interest. Following transfection, the cells were split and diluted in media containing 0.7 mg/ml neomycin (Gibco). Cells were grown until clones could be picked. At least 25 clones from each of the stables were picked, and tested for their suitability as sensor cell lines, by transfecting them with CRE-SEAP and cDNA encoding the M2AchR receptor. Those stables that elicited the maximal signal to noise following activation of the GPCRs were chosen and maintained.

Chimeric G protein cloning: An insert containing rat $G\alpha_s$ cDNA was cut out using the restriction enzymes SalI and HinDIII, and ligated into pcDNA3.1(−) cut with XhoI and HinDIII. The chimeric G proteins with the desired C-terminal amino acid substitutions were prepared by PCR using $G\alpha_s$ as a template. More specifically, $G\alpha_s$ was PCR amplified between an internal EcoRI site and the stop codon, with a 3' HinDIII placed immediately after the stop codon. A different 3' oligonucleotide was used for each $G\alpha_s$ chimera and contained a 39 bp sequence that encoded the substituted amino acids at the C-terminus selected from the donor $G\alpha$ subunit.

M2AchR GPCR cloning: Rat M2AchR receptor was cloned by PCR from cDNA templates (ATCC) and ligated into pcDNA 3.1(−) (Invitrogen) for expression in mammalian cells.

CRE-SEAP Reporter Gene Assay: $0.5 \times 10^5$ HEK-293 cells (ATCC) were seeded into each well of a 96 well plate 24 hours prior to transfection. cDNAs encoding M2AchR, SEAP reporters (Mercury Pathway Profiling System, BD Biosciences), and G protein chimeras were transfected into HEK-293 cells using lipofectamine reagent (Invitrogen) according to the manufacturer's protocols. 20 ng M2AchR cDNA, 20 ng CRE-SEAP cDNA, and 0.5 ng G protein chimera cDNA were transfected into each well of the 96-well plate.

Following transfection, the cells were maintained for 48 hours in 200 ul serum free media containing 10 uM acetylcholine (Sigma). The plates were wrapped in plastic film and heated to 65-70° C. for 2 hours to kill endogenous phosphatases. The plates were then cooled to room temperature, and 100 ul of the supernatant was transferred to a new 96 well plate. 100 ul of substrate solution was added to each well. The substrate solution was 1.2 mM 4-methylumbelliferyl phosphate (Sigma) in 2 M diethanolamine bicarbonate, pH 10.0 (dry ice used to adjust pH). Fluorescence was then measured using a CytoFluor 4000 multi well plate reader (Applied Biosystems).

It will be obvious to those having skill in the art that many changes may be made to the details of the above-described embodiments without departing from the underlying principles of the invention. The scope of the present invention should, therefore, be determined only by the following claims.

The invention claimed is:

1. A method of high throughput screening for G protein-coupled receptor (GPCR) ligands, the method comprising:
providing a cell derived from a mammal, the cell comprising a GPCR of interest, a $G\alpha_s$-based chimera, and a cAMP-dependent reporter gene construct;
administering to the cell a candidate GPCR ligand; and
detecting expression of the cAMP-dependent reporter gene, wherein an increase in the expression of the cAMP-dependent reporter gene is indicative that the candidate GPCR ligand is a GPCR ligand.

2. The method of claim 1, wherein the $G\alpha_s$-based chimera comprises a substitution of at least one of the C-terminal amino acids of the $G\alpha_s$ subunit with the C-terminal amino acids of a $G\alpha$ subunit selected from the group consisting of a $G\alpha_o$ subunit, $G\alpha_z$ subunit, $G\alpha_t$ subunit, $G\alpha_q$ subunit, $G\alpha_{15}$ subunit, $G\alpha_i$ subunit, $G\alpha_k$ subunit, or another G protein alpha subunit.

3. The method of claim 1, wherein the $G\alpha_s$-based chimera is selected from the group consisting of $G\alpha_s$-$G\alpha_i$-5, $G\alpha_s$-$G\alpha_i$-11, $G\alpha_s$-$G\alpha_t$-13, $G\alpha_s$-$G\alpha_t$-13, $G\alpha_s$-$G\alpha_o$-13, $G\alpha_s$-$G\alpha_z$-13, $G\alpha_s$-$G\alpha_{15}$-13, $G\alpha_s$-$G\alpha_k$-5, and $G\alpha_s$-$G\alpha_q$-13.

4. The method of claim 1, wherein the cAMP-dependent reporter gene construct is a CRE-SEAP reporter gene construct.

5. The method of claim 1, wherein an increase in the expression of the cAMP-dependent reporter gene comprises an increase ranging from approximately a 2-fold increase in expression to approximately a 100-fold increase in expression when compared to the expression of the cAMP-dependent reporter gene in the cell before the administration of the candidate GPCR ligand.

6. The method of claim 1, wherein the $G\alpha_s$-based chimera is stably expressed in the cell.

7. The method of claim 1, wherein the GPCR of interest is a GPCR that does not couple with $G\alpha_s$.

8. An isolated peptide comprising a $G\alpha_s$-based chimera, wherein the peptide consists of an amino acid sequence selected from the group consisting of SEQ ID NO: 2, SEQ ID NO: 3, SEQ ID NO: 4, SEQ ID NO: 5, SEQ ID NO: 6, SEQ ID NO: 7, and SEQ ID NO: 8.

9. An isolated nucleotide sequence encoding the isolated peptide of claim 8.

10. An expression vector comprising a nucleotide sequence encoding a $G\alpha_s$-based chimera wherein the nucleotide sequence is selected from at least one of a nucleotide sequences encoding a $G\alpha_s$-based chimera having an amino acid sequence selected from SEQ ID NO: 2, SEQ ID NO: 3, SEQ ID NO: 4, SEQ ID NO: 5, SEQ ID NO: 6, SEQ ID NO: 7, and SEQ ID NO: 8.

11. A method of high throughput screening for GPCR ligands, the method comprising:
providing a cell derived from a mammal, the cell being cotransfected with:
(i) a GPCR that does not couple with $G\alpha_s$,
(ii) a $G\alpha_s$-based chimera selected from the group consisting of $G\alpha_s$-$G\alpha_i$-5, $G\alpha_s$-$G\alpha_i$-11, $G\alpha_s$-$G\alpha_i$-13, $G\alpha_s$-$G\alpha_t$-13, $G\alpha_s$-$G\alpha_o$-13, $G\alpha_s$-$G\alpha_z$-13, $G\alpha_s$-$G\alpha_{15}$-13, $G\alpha_s$-$G\alpha_k$-5, and $G\alpha_s$-$G\alpha_q$-13, and
(iii) a cAMP-dependent reporter gene construct;
administering to the cell a candidate GPCR ligand; and
detecting expression of the cAMP-dependent reporter gene, wherein an increase in the expression of the cAMP-dependent reporter gene is indicative that the candidate GPCR ligand is a GPCR ligand.

12. The method of claim 11, wherein the cAMP-dependent reporter gene construct is a CRE-SEAP reporter gene construct.

13. The method of claim 11, wherein the $G\alpha_s$-based chimera consists of an amino acid sequence selected from the group consisting of SEQ ID NO: 2, SEQ ID NO: 3, SEQ ID NO: 4, SEQ ID NO: 5, SEQ ID NO: 6, SEQ ID NO: 7, and SEQ ID NO: 8.

14. The method of claim 11, wherein the $G\alpha_s$-based chimera is stably expressed in the cell.

15. A method of high throughput screening for GPCR ligands, the method comprising:
providing a cell comprising a GPCR of interest, a $G\alpha_s$-based chimera, and a CRE-SEAP reporter gene construct;
administering to the cell a candidate GPCR ligand; and
detecting expression of the CRE-SEAP reporter gene, wherein an increase in the expression of the CRE-SEAP reporter gene is indicative that the candidate GPCR ligand is a GPCR ligand.

16. The method of claim 15, wherein the cell is derived from a mammal.

17. The method of claim 15, wherein the $G\alpha_s$-based chimera comprises a substitution of at least one of the C-terminal amino acids of the $G\alpha_s$ subunit with the C-terminal amino acids of a $G\alpha$ subunit selected from the group consisting of a $G\alpha o$ subunit, $G\alpha z$ subunit, $G\alpha t$ subunit, $G\alpha q$ subunit, $G\alpha 15$ subunit, $G\alpha i$ subunit, $G\alpha k$ subunit, or another G protein alpha subunit.

18. The method of claim 15, wherein the $G\alpha s$-based chimera is selected from the group consisting of $G\alpha s$-$G\alpha i$-5, $G\alpha s$-$G\alpha i$-11, $G\alpha s$-$G\alpha i$-13, $G\alpha s$-$G\alpha t$-13, $G\alpha s$-$G\alpha o$-13, $G\alpha_s$-$G\alpha_z$-13, $G\alpha_s$-$G\alpha_{15}$-13, $G\alpha_s$-$G\alpha_k$-5, and $G\alpha_s$-$G\alpha_q$-13.

19. The method of claim 15, wherein the $G\alpha_s$-based chimera is stably expressed in the cell.

20. The method of claim 15, wherein the GPCR of interest is a GPCR that does not couple with $G\alpha_s$.

* * * * *

UNITED STATES PATENT AND TRADEMARK OFFICE
CERTIFICATE OF CORRECTION

PATENT NO. : 9,658,208 B2
APPLICATION NO. : 14/367731
DATED : May 23, 2017
INVENTOR(S) : Linda Buck et al.

Page 1 of 1

It is certified that error appears in the above-identified patent and that said Letters Patent is hereby corrected as shown below:

Column 36, Lines 15-16:
"consisting of a Gαo subunit, Gαz subunit, Gαt subunit, Gαq subunit, Gαl5 subunit, Gαi subunit, Gαk subunit, or"
Should read:
--consisting of a $G\alpha_o$ subunit, $G\alpha_z$ subunit, $G\alpha_t$ subunit, $G\alpha_q$ subunit, $G\alpha_{15}$ subunit, $G\alpha_i$ subunit, $G\alpha_k$ subunit, or--.

Column 36, Lines 18-20:
"18. The method of claim 15, wherein the Gαs-based chimera is selected from the group consisting of Gαs-Gαi-5, Gαs-Gαi-11, Gαs-Gαi-13, Gαs-Gαt-13, Gαs-Gαo-13,"
Should read:
--18. The method of claim 15, wherein the $G\alpha_s$-based chimera is selected from the group consisting of $G\alpha_s$-$G\alpha_i$-5, $G\alpha_s$-$G\alpha_i$-11, $G\alpha_s$-$G\alpha_i$-13, $G\alpha_s$-$G\alpha_t$-13, $G\alpha_s$-$G\alpha_o$-13,--.

Signed and Sealed this
Thirty-first Day of October, 2017

Joseph Matal
*Performing the Functions and Duties of the
Under Secretary of Commerce for Intellectual Property and
Director of the United States Patent and Trademark Office*